(12) United States Patent
Allen

(10) Patent No.: US 6,924,128 B2
(45) Date of Patent: Aug. 2, 2005

(54) PACKAGING CELL LINES FOR GENERATION OF HIGH TITERS OF RECOMBINANT AAV VECTORS

(75) Inventor: James M. Allen, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 294 days.

(21) Appl. No.: 09/731,941

(22) Filed: Dec. 6, 2000

(65) Prior Publication Data

US 2003/0175974 A1 Sep. 18, 2003

Related U.S. Application Data

(63) Continuation of application No. 08/564,167, filed as application No. PCT/US95/15892 on Dec. 6, 1995, now abandoned, which is a continuation of application No. 08/480,575, filed on Jun. 7, 1995, now abandoned, and a continuation of application No. 08/350,219, filed on Dec. 6, 1994, now abandoned.

(51) Int. Cl.[7] .................. C12N 15/64; C12N 15/864
(52) U.S. Cl. ............. 435/91.4; 424/93.2; 435/320.1; 435/325; 435/455; 435/456; 435/457; 435/352; 435/366; 435/370; 435/367
(58) Field of Search ............... 435/320.1, 325, 435/455, 456, 91.4, 457, 352, 366, 367, 370, 720.1, 235.1, 964, 69.1; 424/93.2, 93.21, 93.6

(56) References Cited

U.S. PATENT DOCUMENTS

| | | | |
|---|---|---|---|
| 4,797,368 A | 1/1989 | Carter et al. | |
| 5,139,941 A | 8/1992 | Muzyczka et al. | |
| 5,141,742 A | 8/1992 | Brown et al. | |
| 5,173,414 A | 12/1992 | Lebkowski et al. | |
| 5,354,678 A | 10/1994 | Lebkowski et al. | |
| 5,587,308 A | 12/1996 | Carter et al. | |
| 5,622,856 A | 4/1997 | Natsoulis | |
| 5,652,224 A | 7/1997 | Wilson et al. | |
| 5,658,776 A | 8/1997 | Flotte et al. | 435/172.3 |
| 5,658,785 A * | 8/1997 | Johnson | 435/367 |
| 5,786,211 A | 7/1998 | Johnson | |
| 5,837,484 A | 11/1998 | Trempe et al. | 435/69.1 |
| 5,856,152 A | 1/1999 | Wilson et al. | |
| 5,858,775 A | 1/1999 | Johnson | |
| 5,866,552 A | 2/1999 | Wilson et al. | |
| 5,866,696 A | 2/1999 | Carter et al. | |
| 5,871,982 A | 2/1999 | Wilson et al. | |
| 5,872,154 A | 2/1999 | Wilson et al. | |
| 5,989,540 A | 11/1999 | Carter et al. | |
| 5,990,279 A | 11/1999 | Carter et al. | |
| 6,165,781 A | 12/2000 | Carter et al. | |
| 6,174,527 B1 | 1/2001 | Wilson et al. | |
| 6,211,160 B1 | 4/2001 | Wilson et al. | |
| 6,251,677 B1 | 6/2001 | Wilson et al. | |
| 6,251,957 B1 | 6/2001 | Wilson et al. | |
| 6,258,595 B1 | 7/2001 | Gao et al. | |
| 6,261,551 B1 | 7/2001 | Wilson et al. | |
| 6,270,996 B1 | 8/2001 | Wilson et al. | |
| 6,274,354 B1 | 8/2001 | Wilson et al. | |
| 6,281,010 B1 | 8/2001 | Gao et al. | |
| 6,346,415 B1 | 2/2002 | Feldhaus | |
| 6,372,208 B1 | 4/2002 | Wilson et al. | |
| 6,387,368 B1 | 5/2002 | Wilson et al. | |
| 6,399,385 B1 | 6/2002 | Croyle et al. | |
| 6,436,392 B1 | 8/2002 | Engelhardt et al. | |
| 6,475,769 B1 | 11/2002 | Wilson et al. | |
| 6,482,634 B1 | 11/2002 | Wilson et al. | |
| 6,485,966 B2 | 11/2002 | Gao et al. | |
| 6,537,540 B1 | 3/2003 | Burstein et al. | |
| 6,541,258 B2 * | 4/2003 | Allen et al. | 435/455 |
| 6,555,370 B1 | 4/2003 | Lupton | |
| 6,566,118 B1 | 5/2003 | Atkinson et al. | |
| 6,596,535 B1 | 7/2003 | Carter | |
| 6,642,051 B1 | 11/2003 | Lynch et al. | |
| 6,759,237 B1 | 7/2004 | Wilson et al. | |
| 2001/0006955 A1 | 7/2001 | Wilson et al. | |
| 2002/0037867 A1 | 3/2002 | Wilson et al. | |
| 2002/0127582 A1 | 9/2002 | Atkinson et al. | |
| 2002/0160501 A1 | 10/2002 | Atkinson et al. | |
| 2002/0164783 A1 | 11/2002 | Feldhaus | |
| 2002/0182182 A1 | 12/2002 | Wilson et al. | |
| 2002/0197237 A1 | 12/2002 | Engelhardt et al. | |
| 2003/0040101 A1 | 2/2003 | Wilson et al. | |
| 2003/0073232 A1 | 4/2003 | Wilson et al. | |
| 2003/0082145 A1 | 5/2003 | Johnson | |
| 2003/0103939 A1 | 6/2003 | Engelhardt et al. | |

(Continued)

FOREIGN PATENT DOCUMENTS

| | | |
|---|---|---|
| AU | 678867 | 5/1995 |
| AU | 688428 | 5/1995 |
| DE | 4436664 | 7/1996 |
| WO | WO 91/18088 | 11/1991 |
| WO | WO 92/08796 | 5/1992 |

(Continued)

OTHER PUBLICATIONS

Hermonat, P.L. and Muzyczka, N. (1984). "Use of adeno–associated virus as a mammalian DNA cloning vector: Transduction of neomy cin resistance into mammalian tissue culture cells" *Proc. Natl. Acad. Sci. USA* 81:6464–6470.

(Continued)

*Primary Examiner*—Scott D. Priebe
*Assistant Examiner*—Brian Whiteman
(74) *Attorney, Agent, or Firm*—Morrison & Foerster LLP

(57) ABSTRACT

AAV vectors may have utility for gene therapy but heretofore a significant obstacle has been the inability to generate sufficient quantities of such recombinant vectors in amounts that would be clinically useful for human gene therapy application. Stable AAV packaging cell lines have been elusive, mainly due to the activities of Rep protein, which down-regulates its own expression and can negatively affect the host cell. This invention provides packaging systems and processes for packaging AAV vectors that effectively circumvent these problems and that allow for substantially increased packaging efficiency.

22 Claims, 8 Drawing Sheets

U.S. PATENT DOCUMENTS

| | | |
|---|---|---|
| 2003/0103942 A1 | 6/2003 | Burstein et al. |
| 2003/0113295 A1 | 6/2003 | Burstein et al. |
| 2003/0119191 A1 | 6/2003 | Gao et al. |
| 2003/0219735 A1 | 11/2003 | Carter |
| 2004/0052764 A1 | 3/2004 | Hildinger et al. |
| 2004/0057931 A1 | 3/2004 | Wilson et al. |
| 2004/0057932 A1 | 3/2004 | Wilson et al. |
| 2004/0057933 A1 | 3/2004 | Wilson et al. |
| 2004/0062752 A1 | 4/2004 | Walsh et al. |
| 2004/0109950 A1 | 6/2004 | Adams |
| 2004/0110045 A1 | 6/2004 | Rolf |

FOREIGN PATENT DOCUMENTS

| | | |
|---|---|---|
| WO | WO 93/24641 | 12/1993 |
| WO | WO 94/13788 | 6/1994 |
| WO | WO 94/28143 | 12/1994 |
| WO | WO 95/13365 | 5/1995 |
| WO | WO 95/13392 | 5/1995 |
| WO | WO 95/14771 | 6/1995 |
| WO | WO 95/34670 | 12/1995 |
| WO | WO 96/13598 | 5/1996 |
| WO | WO 96/17947 | 6/1996 |
| WO | WO 96/26285 | 8/1996 |
| WO | WO 96/26286 | 8/1996 |
| WO | WO 96/39530 | 12/1996 |
| WO | WO 97/32990 | 12/1997 |
| WO | WO 98/09656 | 3/1998 |
| WO | WO 98/09657 | 3/1998 |
| WO | WO 98/10086 | 3/1998 |
| WO | WO 98/10088 | 3/1998 |
| WO | WO 98/27204 | 6/1998 |
| WO | WO 98/27207 | 6/1998 |
| WO | WO 99/11764 | 3/1999 |
| WO | WO 99/14351 | 3/1999 |
| WO | WO 99/15677 | 4/1999 |
| WO | WO 99/15685 | 4/1999 |
| WO | WO 99/20773 | 4/1999 |
| WO | WO 99/20779 | 4/1999 |
| WO | WO 99/47691 | 9/1999 |
| WO | WO 99/60146 | 11/1999 |
| WO | WO 00/14205 | 3/2000 |
| WO | WO 00/28061 | 5/2000 |
| WO | WO 00/55342 | 9/2000 |
| WO | WO 00/65038 | 11/2000 |
| WO | WO 00/73480 | 12/2000 |
| WO | WO 00/73481 | 12/2000 |
| WO | WO 00/75353 | 12/2000 |
| WO | WO 00/75365 | 12/2000 |
| WO | WO 01/11034 | 2/2001 |
| WO | WO 01/23001 | 4/2001 |
| WO | WO 01/25462 | 4/2001 |
| WO | WO 01/25465 | 4/2001 |
| WO | WO 01/27303 | 4/2001 |
| WO | WO 01/83692 | 11/2001 |
| WO | WO 01/83730 | 11/2001 |
| WO | WO 03/006616 | 1/2003 |

OTHER PUBLICATIONS

Hermonat, P.L. et al. (1984). "Genetics of Adeno–Associated Virus: Isolation and Preliminary Characterization of Adeno–Associated Virus Type 2 Mutants" *J. Virol.* 51(2):329–339.

Hölscher, C. et al. (1994). "Cell Lines Inducibly Expressing the Adeno–Associated Virus (AAV) rep Gene: Requirements for Productive Replication of rep–Negative AAV Mutants"*J. Virol.* 68(11):7169–7177.

Kotin et al. (1990). "Site–specific integration by adeno–associated virus" *Proc. Natl. Acad. Sci. USA* 87:2211–2215.

Kotin et al. (1992). "Characterization of a preferred site on human chromosome 19q for integration of adeno–associated virus DNA by non–homologous recombination," *EMBO J.* 11(13):5071–5078.

Khleif, S.N. et al. (1991). "Inhibition of Cellular Transformation by the Adeno–Associated Virus Rep Gene" *Virology* 181(2):738–741.

Antoni et al. (1991). "Adeno–Associated Virus Rep Protein Inhibits Human Immunodeficiency Virus Type 1 Production in Human Cells" *J. Virol.* (1991) 65(1):396–404.

Arispe, N. et al. (1992). "Intrinsic Anion Channel Activity of the Recombinant First Nucleotide Binding Fold Domain of the Cystic Fibrosis Transmembrane Regulator Protein" *Proc. Natl. Acad. Sci. USA* 89(5):1529–1543.

Berns (1990). *Virology*, Raven Press, New York, pp. 1743–1764.

Blacklow (1988). *Paroviruses and Human Disease*, Pattison, J.R. (ed.), pp. 165–174.

Carter (1989). *Handbook of Paroviruses*, vol. II, CRC Press Boca Raton, FL, pp. 247–284.

Carter (1989). *Handbook of Paroviruses*, vol. I, pp. 169–228.

Carter, B.J. (1992). "Adeno–Associated Virus Vectors", *Current Opinion in Biotechnology* 3(5):533–539.

Carthew, R.W. et al. (1985). "An RNA Polymerase II Transcription Factor Binds to an Upstream Element in the Adenovirus Major Late Promoter" *Cell* 43(2 Pt 1):439–448.

Chatterjee et al. (1991). *Vaccines 91*, Cold Spring Harbor Laboratory Press, pp. 85–89.

Chatterjee, S. et al. (1992). "Dual–Target Inhibition of HIV–1 in Vitro by Means of an Adeno–Associated Virus Antisense Vector" *Science* 258(5087):1485–1488.

Dialog® Abstract of German Patent No. 4436664 (Jul. 4, 1996).

Dialog® Computer Abstract (Biosys File) of Kotin et al. (1989). "Organization of Adeno–Associated Virus DNA in Latently Infected Detroit 6 Cells," *Virology* 170(2):460–467.

Dialog® Computer Abstract (Biosys File) of Samulski et al. (1991). "Targeted Integration of Adeno–Associated Virus AAV into Human Chromosome 19," *EMBO J.* 10(12):3941–3950. One page total.

Dialog® Computer Abstract (Biosys File) of Srivastava et al. (1983). "Nucleotide Sequence and Organization of the Adeno–Associated Virus 2 Genome," *J. Virol.* 45(2):555–564.

Egan, M. et al. (1992). "Defective Regulation of Outwardly Rectifying Cl– Channels by Protein Kinase A Corrected by Insertion of CFTR," *Nature* 358(6387):581–584.

Flotte, T.R. et al. (1992), "Gene Expression from Adeno–Associated Virus Vectors in Airway Epithelial Cells" *Am. J. Repir. Cell. Mol. Biol.* 7(3):349–356.

Flotte, T.R. et al. (1993). "Expression of the Cystic Fibrosis Transmembrane Conductance Regulator from a Novel Adeno–Associated Virus Promoter" *J. Biol. Chem.* 268:3781–3790.

Flotte, T. R. et al. (1993). "Stable in Vivo Expression of the Cystic Fibrosis Transmembrane Conductance Regulator with an Adeno–Associated Virus Vector" *Proc. Natl. Acad. Sci. USA* 90(22):10613–10167.

Flotte et al. (1995). "An Improved System for Packaging Recombinant Adeno–Associated Virus Vectors Capable of In Vivo Transduction," *Gene Therapy* 2(1):29–37.

Hamer, D.H. and Walling, M. (1982). "Regulation in Vivo of a Cloned Mammalian Gene: Cadmium Induces the Transcription of a Mouse Metallothionein gene in SV40 Vectors" *J. Mol. Appl. Genet.* 1(4):273–288.

Kaplitt, M.G. et al. (1994). "Long–Term Gene Expression and Phenotypic Correction Using Adeno–Associated Virus Vectors in the Mammalian Brain" *Nature Genetics* 8:148–154.

Labow, M.A. et al. (1987). "Adeno–Associated Virus Gene Expression Inhibits Cellular Transformation by Heterologous Genes" *Mol. Cell. Biol.* 7(4):1320–1325.

Labow et al. (1986)., "Positive and Negative Autoregulation of the Adeno–Associated Virus Type 2 Genome" *Virology* 60(1):251–258.

Labow et al. (1988). "The Adeno–Associated Virus rep Gene Inhibits Replication of an Adeno–Associated Virus/Simian Virus 40 Hybrid Genome in Cos–7 Cells," *Virology*, 62(5):1705–1712.

LaFace, D. et al. (1988). "Gene Transfer into Hematopoietic Progenitor Cells Mediated by an Adeno–Associated Virus Vector" *Virology* 162(2):483–486.

Laughlin, C.A. et al. (1979). "Spliced Adenovirus–Associated Virus RNA" *Proc. Natl. Acad. Sci. USA* 76(11):5567–5571.

Laughlin, C.A. et al. (1983). "Cloning of Infectious Adeno–Associated Virus Genomes in Bacterial Plasmids" *Gene* 23(1):65–73.

Lebkowski, J.S. et al. (1988). "Adeno–Associated Virus: A Vector System for Efficient Introduction and Integration of DNA into a Variety of Mammalian Cell Types" *Mol. Cell. Biol.* 8(10):3988–3996.

McLaughlin, S.K. et al. (1988). "Adeno–Associated Virus General Transduction Vectors: Analysis of Proviral Structures" *J. Virol.* 62(6):1963–1973.

Mendelson, E. et al. (1988). "Expression and Rescue of a Nonselected Marker from an Integrated AAV Vector" *Virology* 166(1):154–164.

Muro–Cacho et al. (1992). "Gene–Transfer in Human Lymphocytes Using a Vector Based on Adeno–Associated Virus" *J. Immunotherapy* 11(4):231–237.

Muzyczka, N. (1992). "Use of Adeno–Associated Virus as a General Transduction Vector for Mammalian Cells" *Current Topics in Microbiology and Immunology* 158:97–129.

Rich, D.P. et al. (1991). "Effect of Deleting the R Domain on CFTR–Generated Chloride Channels" *Science* 253(5016):205–207.

Rittner et al. (1992). "Adeno–Associated Virus Type 2–Mediated Inhibition of Human Immunodeficiency Virus Type 1 (HIV–1) Replication: Involvement of $p78^{rep}/p68^{rep}$ and the HIV–1 Long Terminal Repeat," *J. Gene Virology* 73:2977–2981.

Riordan, J.R. et al. (1989). "Identification of the Cystic Fibrosis Gene: Cloning and Characterization of Complementary DNA" *Science* 245:1066–1073.

Rommens, J.M. et al. (1989). "Identification of the Cystic Fibrosis Gene: Chromosome Walking and Jumping" *Science* 245(4922):1059–1065.

Rose, J. A. (1974). "Parvovirus Reproduction," Chapter 1 *In Comprehensive Virology* pp. 1–61.

Samulski, R.J. et al. (1982). "Cloning of Adeno–Associated Virus into pBR322: Rescue of Intact Virus from the Recombinant Plasmid in Human Cells" *Proc. Natl. Acad. Sci. USA* 79(6):2077–2081.

Samulski, R.J. et al. (1987). "A Recombinant Plasmid from which an Infectious Adeno–Associated Virus Genome can be Excised in Vitro and its use to Study Viral Replication" *J. Virol.* 61(10):3096–3101.

Samulski, R.J. et al. (1989). "Helper–Free Stocks of Recombinant Adeno–Associated Viruses: Normal Integration does not Require Viral Gene Expression" *J. Virol.* 63(9):3822–3828.

Samulski et al. (1991). "Targeted Integration of Adeno–Associated Virus (AAV) into Human Chromosome 19," *EMBO J.* 10(12):3941–3950.

Senapathy, P. and Carter, B.J. (1984). "Molecular Cloning of Adeno–Associated Virus Variant Genomes and Generation of Infectious Virus by Recombination in Mammalian Cells" *J. Biol. Chem.* 259(7):4661–4666.

Sheppard, D.N. et al. (1994). "The Amino–Terminal Portion of CFTR Forms a Regulated Cl–Channel" *Cell* 76(6):1091–1098.

Srivastava, A. et al. (1983). "Nucleotide Sequence and Organization of the Adeno–Associated Virus 2 Genome" *J. Virol.* 45(2):555–564.

Srivastava, C.H. et al. (1989). "Construction of a Recombinant Human Parvovirus B19: Adeno–Associated Virus 2 (AAV) DNA Inverted Terminal Repeats are Functional in an AAV–B19 Hybrid Virus" *Proc. Natl. acad. Sci. USA* 86(20):8078–8082.

Tratschin, J.D. et al. (1984). "A Human Parvovirus, Adeno–Associated Virus, as a Eucaryotic Vector: Transient Expression and Encapsidation of the Procaryotic Gene for Chloramphenicol Acetyltransferase" *Mol. Cell. Biol.* 4(10):2072–2081.

Tratschin, J.D. et al. (1985). "Adeno–Associated Virus Vector for High–Frequency Integration, Expression, and Rescue of Genes in Mammalian Cells" *Mol. Cell. Biol.* 5(11):3151–3260.

Tratschin, J.D. et al. (1986). "Negative and Positive Regulation in Trans of Gene Expression from Adeno–Associated Virus Vectors in Mammalian Cells by a Viral Rep Gene Product" *Mol. Cell. Biol.* 6(8):2884–2894.

Tratschin, J.D. et al. (1984). "Genetic Analysis of Adeno–Associated Virus: Properties of Deletion Mutants Constructed in Vitro and Evidence for an Adeno–Associated Virus Replication Function" *J. Virol.* 51(3):611–619.

Trempe, J.P. et al. (1987). "Characterization of Adeno–Associated Virus Rep Proteins in Human Cells by Antibodies Raised Against Rep Expressed in *Escherichia coli* " *Virology* 161:18–28.

Vincent et al. (1990). *Vaccines 90*, Cold Spring Harbor Laboratory Press, pp. 353–359.

Walsh, C.E. et al. (1992). "Regulated High Level Expression of a Human Gamma–Globin Gene Introduced into Erythroid Cells by an Adeno–Associated Virus Vector" *Proc. Natl. Acad. Sci. USA* 89(15):7257–7261.

Winocour et al. (1992). "Modulation of the Cellular Phenotype by Integrated Adeno–Associated Virus" *Virology* 190:316–329.

Wong et al. (1991). *Vaccines 91*, Cold Spring Harbor Laboratory Press, pp. 183–189.

Yang, Q. et al. (1994). "Characterization of Cell Lines that Inducibly Express the Adeno–Associated Virus Rep Proteins" *J. Virol.* 68(8):4847–4856.

\* cited by examiner

| | | | | |
|---:|---:|:-:|:-:|:-:|:-:|
| WT AAV | − | − | − | + |
| Adenovirus | − | − | + | + |
| AAV CMV hygro | − | + | + | + |
| Lanes | 1 | 2 | 3 | 4 |

1.488 kb →

PACKAGING CELL LINES FOR GENERATION OF HIGH TITERS OF RECOMBINANT AAV VECTORS

This application is a continuation of U.S. patent application Ser. No. 08/564,167, filed Dec. 4, 1995, now abandoned, which is the U.S. National Phase of International Application PCT/US95/15892, filed on Dec. 6, 1995, which is a continuation of U.S. patent application Ser. No. 08/480,575, which was filed Jun. 7, 1995, now abandoned, and is a continuation of U.S. patent application Ser. No. 08/350,219, which was filed Dec. 6, 1994, now abandoned.

TECHNICAL FIELD OF THE INVENTION

This invention relates to gene therapy, and more specifically to materials and methods used for the generation of high titers of recombinant AAV vectors for use in gene therapy procedures.

BACKGROUND

AAV vectors may have utility for gene therapy but heretofore a significant obstacle has been the inability to generate sufficient quantities of such recombinant vectors in amounts that would be clinically useful for human gene therapy application. This is a particular problem for in vivo applications such as direct delivery to the lung.

Adeno-associated virus (AAV) vectors are among a small number of recombinant virus vector systems which have been shown to have utility as in vivo gene transfer agents (reviewed in Carter, 1992, *Current Opinion in Biotechnology*, 3:533–539; Muzcyzka, 1992, *Curr. Top. Microbiol. Immunol.* 158:97–129) and thus are potentially of great importance for human gene therapy. AAV vectors are capable of high-frequency stable DNA integration and expression in a variety of cells including cystic fibrosis (CF) bronchial and nasal epithelial cells (see, e.g., Flotte et al., 1992a,*Am. J. Respir. Cell Mol. Biol.* 7:349–356; Egan et al., 1992, *Nature,* 358:581–584; Flotte et al., 1993a, *J. Biol. Chem.* 268:3781–3790; and Flotte et al., 1993b, *Proc. Natl. Acad. Sci. USA,* 93:10163–10167); human bone marrow-derived erythroleukemia cells (see, e.g., Walsh et al., 1992, *Proc. Natl. Acad. Sci. USA,* 89:7257–7261); and several others. AAV may not require active cell division for stable expression which would be a clear advantage over retroviruses, especially in tissue such as the human airway epithelium where most cells are terminally differentiated and non-dividing.

AAV is a defective parvovirus that grows only in cells in which certain functions are provided by a co-infecting helper virus (see FIG. 1). General reviews of AAV may be found in Carter, 1989, *Handbook of Parvoviruses*, Vol. I, pp. 169–228, Berns, 1990, *Virology,* pp. 1743–1764, Raven Press, (New York). Examples of co-infecting viruses that provide helper functions for AAV growth and replication are adenoviruses, herpesviruses and in some cases poxviruses such as vaccinia. The nature of the helper function is not entirely known but appears to be some indirect effect of the helper virus which renders the cell permissive for AAV replication. This belief is supported by the observation that in certain cases AAV replication may occur at a low level of efficiency in the absence of helper virus co-infection if the cells are treated with agents that are either genotoxic or that disrupt the cell cycle.

Although AAV may replicate to a limited extent in the absence of helper virus in certain unusual conditions, as noted above, the more general result is that infection of cells with AAV in the absence of helper functions results in integration of AAV into the host cell genome. The integrated AAV genome may be rescued and replicated to yield a burst of infectious progeny AAV particles if cells containing an integrated AAV provirus are superinfected with a helper virus such as adenovirus. Because the integration of AAV appears to be an efficient event, this suggested that AAV would be a useful vector for introducing genes into cells for stable expression for uses such as human gene therapy.

AAV has a very broad host range with neither any obvious species nor tissue specificity and will replicate in virtually any cell line of human, simian or rodent origin provided an appropriate helper is present. AAV is ubiquitous and has been isolated from a wide variety of animal species including most mammalian and several avian species.

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector because most of the other viral systems proposed for this application such as retroviruses, adenoviruses, herpesviruses, or poxviruses are disease-causing viruses.

AAV particles are comprised of a protein capsid having three capsid proteins, VP1, VP2, and VP3, and enclosing a DNA genome. The AAV DNA genome is a linear single-stranded DNA molecule having a molecular weight of about $1.5 \times 10^6$ daltons or approximately 4680 nucleotides long. Strands of either complementary sense, "plus" or "minus" strands, are packaged into individual particles but each particle has only one DNA molecule. Equal numbers of AAV particles contain either a plus or minus strand. Either strand is equally infectious and replication occurs by conversion of the parental infecting single strand to a duplex form and subsequent amplification of a large pool of duplex molecules from which progeny single strands are displaced and packaged into capsids. Duplex or single-strand copies of AAV genomes inserted into bacterial plasmids or phagemids are infectious when transfected into adenovirus-infected cells, and this has allowed the study of AAV genetics and the development of AAV vectors.

The AAV2 genome has two copies of a 145-nucleotide-long ITR (inverted terminal repeat), one on each end of the genome, and a unique sequence region of about 4470 nucleotides long (Srivastava et al., 1983, *J. Virol.,* 45:555–564) that contains two main open reading frames for the rep and cap genes (Hermonat et al.,*J. Virol.* 51:329–339; Tratschin et al., 1984a, *J. Virol.,* 51:611–619). The unique region contains three transcription promoters p5, p19, and p40 (Laughlin et al., 1979, *Proc. Natl. Acad. Sci. USA,* 76:5567–5571) that are used to express the rep and cap genes. The ITR sequences are required in cis and are sufficient to provide a functional origin of replication (ori) and also are sufficient to provide signals required for integration into the cell genome as well as for efficient excision and rescue from host cell chromosomes or from recombinant plasmids. In addition it has been shown that the ITR can function directly as a transcription promoter in an AAV vector (Flotte et al., 1993, vide supra).

The rep and cap genes are required in trans to provide functions for replication and encapsidation of viral genome respectively. The rep gene is expressed from two promoters, p5 and p19. Transcription from p5 yields an unspliced 4.2 kb mRNA which encodes a protein, Rep78, and a spliced 3.9 kb mRNA which encodes a protein, Rep68. Transcription from p19 yields an unspliced mRNA which encodes Rep52 and a spliced 3.3 kb mRNA which encodes Rep40. Thus, the four Rep proteins all comprise a common internal region sequence but differ with respect to their amino and carboxyl terminal regions. Only Rep78 and Rep68 are required for AAV duplex DNA replication, but Rep52 and Rep40 appear to be needed for progeny, single-strand DNA accumulation. Mutations in Rep78 and Rep68 are phenotypically Rep− whereas mutations affecting only Rep52 and Rep40 are Rep+ but Ssd−. Rep68 and Rep78 bind specifically to the hairpin conformation of the AAV ITR and possess several enzyme activities required for resolving replication at the AAV termini. Rep52 and Rep40 have none of these properties.

The Rep proteins, primarily Rep78 and Rep68 exhibit several pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.,* 7:1320–1325; Khleif et al., *Virology,* 181:738–741). The AAV p5 promoter is negatively autoregulated by Rep78 or Rep68 (Tratschin et al., 1986, *Mol. Cell. Biol.* 6:2884–2894). Because of the inhibitory effects of expression of rep on cell growth, constitutive expression of rep in cell lines has not been readily achieved. For example, Mendelson et al. (1988, *Virology,* 166:154–165) reported a very low level expression of some Rep proteins in certain cell lines after stable integration of AAV genomes.

The proteins VP1, VP2, and VP3 all share a common overlapping sequence but differ in that VP1 and VP2 contain additional amino terminal sequence. All three are coded from the same cap gene reading frame expressed from a spliced 2.3 kb mRNA transcribed from the p40 promoter. VP2 and VP3 are generated from the same mRNA by use of alternate initiation codons. VP1 is coded from a minor mRNA using 3' donor site that is 30 nucleotides upstream from the 3' donor used for the major mRNA that encodes VP2 and VP3. VP1, VP2, and VP3 are all required for capsid production. Mutations which eliminate all three proteins (Cap−) prevent accumulation of single-strand progeny AAV DNA whereas mutations in the VP1 amino-terminus (Lip−, Inf−) permit single-strand production but prevent assembly of stable infectious particles.

The genetic analysis of AAV that was described above was based upon mutational analysis of AAV genomes that were molecularly cloned into bacterial plasmids. In early work, molecular clones of infectious genomes of AAV were constructed by insertion of double-strand molecules of AAV into plasmids by procedures such as GC tailing (Samulski et al., 1982, *Proc. Natl. Acad. Sci. USA,* 79:2077–2081), addition of synthetic linkers containing restriction endonuclease (Laughlin et al., 1983, *Gene,* 23:65–73) or by direct, blunt-end ligation (Senapathy & Carter, 1984, *J. Biol. Chem.,* 259:4661–4666). It was then shown that transfection of such AAV recombinant plasmids into mammalian cells that were also infected with an appropriate helper virus, such as adenovirus, resulted in rescue and excision of the AAV genome free of any plasmid sequence and replication of the rescued genome and generation of a yield of progeny infectious AAV particles. This provided the basis for performing genetic analysis of AAV as summarized above and permitted construction of AAV transducing vectors.

Based on the genetic analysis, the general principles of AAV vector construction were defined as reviewed recently (Carter, 1992, *Current Opinions in Biotechnology,* 3:533–539; Muzyczka, 1992, *Current Topics in Microbiology and Immunology,* 158:97–129). AAV vectors are constructed in AAV recombinant plasmids by substituting portions of the AAV coding sequence with foreign DNA to generate a vector plasmid. In the vector plasmid, the terminal (ITR) portions of the AAV sequence must be retained intact because these regions are required in cis for several functions including excision from the plasmid after transfection, replication of the vector genome and integration and rescue from a host cell genome. The vector can then be packaged into an AAV particle to generate an AAV transducing virus by transfection of the vector plasmid into cells that are infected by an appropriate helper virus such as adenovirus or herpesvirus. In order to achieve replication and encapsidation of the vector genome into AAV particles, the vector plasmid must be complemented for any AAV functions required in trans, namely rep and cap, that were deleted in construction of the vector plasmid.

There are at least two desirable features of any AAV vector that is designed for use in human gene therapy. First, the transducing vector must be generated at sufficiently high titers that it is practicable as a delivery system. This is especially important for gene therapy stratagems aimed at in vivo delivery of the vector. It is likely that for many desirable applications of AAV vectors, such as treatment of cystic fibrosis by direct in vivo delivery to the airway, the required dose of transducing vector may be in excess of $10^{10}$. Secondly, the vector preparations must be free of wild-type AAV virus. The attainment of high titers of AAV vectors has been difficult for several reasons including preferential encapsidation of wild-type AAV genomes if they are present or generated by recombination, and the inability to generate sufficient complementing functions such as rep or cap. Useful cell lines expressing such complementing functions have not been generated, in part, because of several inhibitory functions of the rep gene.

The first AAV vectors that were described contained foreign reporter genes such as neo or cat or dhfr that were expressed from AAV transcription promoters or an SV40 promoter (Tratschin et al., 1984b, *Mol. Cell. Biol.* 4:2072–2081; Hermonat & Muzyczka, 1984, *Proc. Natl. Acad. Sci. USA,* 81:6466–6470; Tratschin et al., 1985, *Mol. Cell. Biol.* 5:3251–3260; McLaughlin et al., 1988, *J. Virol.,* 62:1963–1973; Lebkowski et al., 1988 *Mol. Cell. Biol.,* 7:349–356). These vectors were packaged into AAV-transducing particles by co-transfection into adenovirus-infected cells together with a second packaging plasmid that contained the AAV rep and cap genes expressed from the natural wild-type AAV transcription promoters. In an attempt to prevent packaging of the packaging plasmid into AAV particles several approaches were taken. In some cases, (Hermonat & Muzyczka, 1984; McLaughlin et al., 1988) the packaging plasmid had inserted a large region of bacteriophage lambda DNA within the AAV sequence to generate an oversized genome that could not be packaged. In other cases, (Tratschin et al., 1984b; Tratschin et al., 1985, Lebkowski et al., 1988), the packaging plasmid had deleted the ITR regions of AAV in order that it could not be excised and replicated and thus could not be packaged. All of these approaches failed to prevent generation of particles containing wild-type AAV DNA and also failed to generate effective high titers of AAV transducing particles. Indeed titers of not more than $10^4$ ml were cited by Hermonat & Muzyczka, 1984. The production of wild-type AAV particles in these studies was probably due to the presence of overlapping homology between AAV sequences present in the vector and packaging plasmids. It was shown by Senapathy and Carter (1984, *J. Biol. Chem.* 259:4661–4666) that the degree of recombination in such a system is approximately equivalent to the degree of sequence overlap. It was suggested in a review of the early work (Carter 1989, *Handbook of Parvoviruses*, Vol. II, pp. 247–284, CRC Press, Boca Raton, Fla.) that titers of $10^6$ per ml might be obtained, but this was based on the above-cited studies in which large amounts of wild-type AAV contaminated the vector preparation. Such vector preparations containing wild-type AAV are not useful human gene therapy. Furthermore, these early vectors exhibited low transduction efficiencies and did not transduce more than 1 or 2% of cells in cultures of various human cell lines even though the vectors were supplied at multiplicities of up to 50,000 particles per cell. This may have reflected in part the contamination with wild-type AAV particles and the presence of the AAV rep gene in the vector. Furthermore, Samulski et al. (1989, *J. Virol.* 63:3822–3828) showed that the presence of wild-type AAV significantly enhanced the yield of packaged vector. Thus, in packaging systems where the production of wild-type AAV is eliminated, the yield of packaged vector may actually be decreased. Nevertheless, for use in any human clinical application it will be essential to eliminate production of wild-type AAV.

Additional studies (McLaughlin et al., 1988; Lebkowski et al., 1988) to generate AAV vectors which did not contain the AAV rep or cap gene still met with generation of wild-type AAV and still produced very low transduction frequencies on human cell lines. Thus, McLaughlin et al., 1988 reported that AAV rep– cap– vectors containing the neo gene packaged with the same packaging plasmid used earlier by Hermonat & Muzyczka (1984) still contained wild-type AAV. As a consequence it was only possible to use this virus at a multiplicity of 0.03 particles per cell (i.e., 300 infectious units per 10,000 cell) to avoid double hits with vector and wild-type particles. When the experiment was done in this way, by infecting 32,000 cells with 1000 infectious units, an average of 800 geneticin-resistant colonies was obtained. Although this was interpreted as demonstrating the virus was capable of yielding a transduction frequency of 80%, in fact only 2.5% of the cells were transduced. Thus the effectively useful titer of this vector was limited. Furthermore, this study did not demonstrate that the actual titer of the vector preparation was any higher than those obtained previously by Hermonat & Muzyczka (1984). Similarly, Lebkowski et al., 1988, packaged AAV vectors which did not contain either a rep or cap gene and used an ori– packaging plasmid pBa1A identical to that used earlier by Tratschin et al., (1984b, 1985) and reported transduction frequencies that were similarly low, in that for several human cell lines not more than 1% of the cells could be transduced to geneticin resistance even with their most concentrated vector stocks. Lebkowski et al., (1988) did not report the actual vector titers in a meaningful way but the biological assays showing not more than 1% transduction frequency when $5 \times 10^6$ cells were exposed to three ml of vector preparation indicates that the titer was less than $2 \times 10^4$. Also, the pBa1 packaging plasmid contains overlapping homology with the ITR sequence in the vector and leads to generation by recombination of wild-type AAV.

Laface et al., (1988) used the same vector as that used by Hermonat & Muzyczka (1984) prepared in the same way and obtained a transduction frequency of 1.5% in murine bone marrow cultures again showing very low titer.

Samulski et al., (1987, *J. Virol.*, 61:3096–3101) constructed a plasmid called pSub201 which was an intact AAV genome in a bacterial plasmid but which had a deletion of 13 nucleotides at the extremity of each ITR and thus was rescued and replicated less efficiently than other AAV plasmids that contained the entire AAV genome. Samulski et al. (1989, *J. Virol.*, 63:3822–3828) constructed AAV vectors based on pSub201 but deleted for rep and cap and containing either a hyg or neo gene expressed from an SV40 early gene promoter. They packaged these vectors by co-transfection with a packaging plasmid called pAAV/Ad which consisted of the entire AAV nucleotide sequence from nucleotide 190 to 4490 enclosed at either end with one copy of the adenovirus ITR. In this packaging plasmid the AAV rep and cap genes were expressed from the natural AAV promoters p5, p19 and p40. The function of the adenovirus ITR in pAAV/Ad was thought to be to enhance the expression level of AAV capsid proteins. However, rep is expressed from its homologous promoter and is negatively regulated and thus its expression is limited. Using their encapsidation system Samulski et al., 1989, generated AAV vector stocks that were substantially free of wild-type AAV but had transducing titers of only $3 \times 10^4$ hygromycin-resistant units per ml of supernatant. When a wild-type AAV genome was used in the packaging plasmid the titer of the AAV vector prep was increased to $5 \times 10^4$. The low titer produced in this system thus appears to have been due in part to the defect in the ITR sequences of the basic pSub201 plasmid used for vector construction and in part due to limiting expression of AAV genes from pAAV/Ad. In an attempt to increase the titer of the AAVneo vector preparation, Samulski et al., 1989, generated vector stocks by transfecting, in bulk, thirty 10-cm dishes of 293 cells and concentrating the vector stock by banding in CsCl. This produced an AAVneo vector stock containing a total of $10^8$ particles as measured by a DNA dot-blot hybridization assay. When this vector stock was used at multiplicities of up to 1,000 particles per cell, a transduction frequency of 70% was obtained. This suggests that the particle-to-transducing ratio is about 500 to 1,000 particles since at the ratio of one transducing unit per cell the expected proportion of cells that should be transduced is 63% according to the Poisson distribution.

Although the system of Samulski et al., 1989, using the vector plasmid pSub201 and the packaging plasmid pAAV/Ad did not have overlapping AAV sequence homology between the two plasmids, there is overlapping homology at the XbaI sites and recombination of these sites leads to generation of complete wild-type AAV. That is, although overlapping homology of AAV sequence is not present, the complete AAV sequence is contained within the two plasmids, and thus recombination can generate wild-type AAV, which is undesirable. That this class of recombination occurs in AAV plasmids was shown by Senapathy & Carter (1984, *J. Biol. Chem.* 259:4661–4666). Therefore, because of the problems of low titer and ability to generate wild-type recombinants, the system described by Samulski et al., 1989, does not have utility for human gene therapy.

Several other reports have described AAV vectors. Srivastava et al., (1989, *Proc. Natl. Acad. Sci. USA*, 86:8078–8082) described an AAV vector based on the pSub201 plasmid of Samulski et al., (1987), in which the coding sequences of AAV were replaced with the coding sequences of another parvovirus, B19. This vector was packaged into AAV particles using the pAAV/Ad packaging plasmid and generated a functional vector, but titers were not reported. This system was based on pSub201 and thus suffers from the defect described above for this plasmid. Second, the vector and the packaging plasmid both contained overlapping AAV sequences (the ITR regions) and thus recombination to give contaminating wild-type virus is highly likely.

Chatterjee et al. (1991, *Vaccines* 91, Cold Spring Harbor Laboratory Press, pp. 85–89), Wong et al. (1991 *Vaccines* 91, Cold Spring Harbor Laboratory Press, pp. 183–189), and Chatterjee et al. (1992, *Science,* 258:1485–1488) describe AAV vectors designed to express antisense RNA directed against infectious viruses such as HIV or Herpes simplex virus. However, these authors did not report any titers of their AAV vector stocks. Furthermore, they packaged their vectors using an Ori− packaging plasmid analogous to that used by Tratschin et al. (1984b, 1985) containing the Ba1A fragment of the AAV genome and therefore their packaging plasmid contained AAV vector sequences that have homology with AAV sequences that were present in their vector constructs. This will also lead to generation of wild-type AAV. Thus, Chatterjee et al., and Wong et al., used a packaging system known to give only low titer and which can lead to generation of wild-type AAV genomes because of the overlapping homology in the vector and packaging sequences.

Other reports have described the use of AAV vectors to express genes in human lymphocytes (Muro-Cacho et al., 1992, *J. Immunotherapy,* 11:231–237) or a human erythroid leukemia cell line (Walsh et al., 1992, *Proc. Natl. Acad. Sci. USA,* 89:7257–7261) with vectors based on the pSub201 vector plasmid and pAAV/Ad packaging plasmid. Again, titers of vector stocks were not reported and were apparently low because a selective marker gene was used to identify those cells that had been successfully transduced with the vector.

Transduction of human airway epithelial cells, grown in vitro from a cystic fibrosis patient, with an AAV vector expressing the selective marker gene neo from the AAV p5 promoter was reported (Flotte et al., 1992, *Am. J. Respir. Cell. Mol. Biol.* 7:349–356). In this study the AAVneo vector was packaged into AAV particles using the pAAV/Ad packaging plasmid. Up to 70% of the cells in the culture could be transduced to geneticin resistance and the particle-to-transducing ratio was similar to that reported by Samulski et al., (1989). Thus to obtain transduction of 70% of the cells, a multiplicity of up to several hundred vector particles per cell was required. Transduction of human airway epithelial cells in in vitro culture using an AAV transducing vector that expressed the CFTR gene from the AAV ITR promoter showed that the cells could be functionally corrected for the electrophysiological defect in chloride channel function that exists in cells from cystic fibrosis patients (Egan et al., *Nature,* 1992, 358:581–584; Flotte et al., *J. Biol. Chem.* 268:3781–3790).

The above-cited studies suggest that AAV vectors may have potential utility as vectors for treatment of human disease by gene therapy. However, the ability to generate sufficient amounts of AAV vectors has been a severe limitation on the development of human gene therapy using AAV vectors. One aspect of this limitation is that there have been very few studies using AAV vectors in in vivo animal models (see, e.g., Flotte et al., 1993b; and Kaplitt et al., 1994, Nature Genetics 8:148–154). This is generally a reflection of the difficulty associated with generating sufficient amounts of AAV vector stocks having a high enough titer to be useful in analyzing in vivo delivery and gene expression. One of the limiting factors for AAV gene therapy has been the relative inefficiency of the vector packaging systems that have been used. Because of the lack of cell lines expressing the AAV trans complementing functions, such as rep and cap, packaging of AAV vectors has been achieved in adenovirus-infected cells by co-transfection of a packaging plasmid and a vector plasmid. The efficiency of this process may be limited by the efficiency of transfection of each of the plasmid constructs, and by the level of expression of Rep proteins from the packaging plasmids described to date. Each of these problems appears to relate to the biological activities of the AAV Rep proteins. In addition, as noted above, all of the packaging systems described above have the ability to generate wild-type AAV by recombination.

The lack of cell lines stably expressing functional Rep apparently reflects a cytotoxic or cytostatic function of Rep as shown by the inhibition by Rep of neo-resistant colony formation (Labow et al., 1987; Trempe et al., 1991). This also appears to relate to the tendency of Rep to reverse the immortalized phenotype in cultured cells, which has made the production of cell lines stably expressing functional Rep extremely difficult. Several attempts to generate cell lines expressing Rep have been made. Mendelson et al., (1988, *Virology,* 166:154–165) reported obtaining in one cell line some low level expression of AAV Rep52 protein but no Rep78 or Rep68 protein after stable transfection of HeLa or 293 cells with plasmids containing an AAV rep gene. Because of the absence of Rep78 and Rep68 proteins, vector could not be produced in the cell line. Another cell line made a barely detectable amount of Rep78 which was nonfunctional.

Vincent et al. (1990, *Vaccines* 90, Cold Spring Harbor Laboratory Press, pp. 353–359) attempted to generate cell lines containing the AAV rep and cap genes expressed from the normal AAV promoters, but these attempts were not successful either because the vectors were contaminated with a 100-fold excess of wild-type AAV particles or because the vectors were produced at only very low titers of less than $4 \times 10^3$.

In an alternate approach, Lebkowski et al. (U.S. Pat. No. 5,173,414, issued Dec. 22, 1992) constructed cell lines containing AAV vectors in an episomal plasmid. These cell lines could then be infected with adenovirus and transfected with the trans complementing AAV functions rep and cap to generate preparations of AAV vector. It is claimed that this allows higher titers of AAV stocks to be produced. However, in the examples shown, the only information relative to titer that is shown is that one human cell line, K562, could be transduced at efficiencies of only 1% or less, which does not indicate high titer production of any AAV vector. In this system the vector is carried as an episomal (unintegrated construct), and it is stated that integrated copies of the vector are not preferred. In a subsequent patent (U.S. Pat. No. 5,354,678, issued Oct. 11, 1994), Lebkowski et al. introduce rep and cap genes into the cell genome but the method again requires the use of episomal AAV transducing vectors comprising an Epstein-Barr virus nuclear antigen (EBNA) gene and an Epstein-Barr virus latent origin of replication; and, again, the only information relative to titer showed a fairly low titer.

The approach to packaging of AAV vectors described by Lebkowski et al., 1992, has several undesirable aspects. First, maintaining the vector as an unintegrated, high copy number episomal plasmid in a cell line is not desirable because the copy number per cell cannot be rigorously controlled and episomal DNA is much more likely to undergo rearrangement leading to production of defective vectors. Secondly, in this system, the vector must still be packaged by infecting the cell line with adenovirus and introducing a plasmid containing the AAV rep and cap genes. The plasmid used by Lebkowski et al., 1992, again was pBa1 which, as noted above, has overlapping homology with the vector ITR sequences and will result in generation of wild-type AAV. Third, in the pBa1 packaging plasmid used by Lebkowski et al., 1988, 1992, the rep gene is expressed off its homologous p5 promoter and is thus negatively autoregulated and therefore rep expression is likely to be limited.

The problem of suboptimal levels of rep expression after plasmid transfection may relate to another biological activity of these proteins. There is evidence (Tratschin et al., 1986, *Mol. Cell. Biol.* 6:2884–2894) that AAV-Rep proteins down-regulate their own expression from the AAV-p5 promoter which has been used in all of the previously described packaging constructs such as pAAV/Ad (Samulski et al., 1989) or pBa1 (Lebkowski et al., 1988, 1992).

Another attempt to develop cell lines expressing functional rep activity was recently published by Hölscher et al. (1994, *J. Virol.* 68:7169–7177). They described the generation of cell lines in which rep was placed under control of a glucocorticoid-responsive MMTV promoter. Although they observed particle formation, the particles were apparently noninfectious. Additional experiments indicated that the defect was quite fundamental; namely, there was virtually no accumulation of single-stranded rAAV DNA in the cells. Production of infectious particles required an additional transient transfection with constitutive highly-expressed rep constructs (i.e. they had to "add back" rep activity to cells that were supposed to be able to provide it themselves).

SUMMARY OF THE INVENTION

One of the basic challenges for gene therapy has been the development of strategies for transduction of cells and tissues which cannot be easily manipulated ex vivo or which are not actively dividing. AAV vectors can achieve in vivo gene transfer in the respiratory tract, for example, but high titers are critical so as to allow for the delivery of sufficiently high multiplicity of vector in as small a volume as possible. This makes optimal packaging methodology of central importance in determining the feasibility of an AAV-based gene therapy. Stable, helper-free AAV packaging cell lines have been elusive, mainly due to the activities of Rep protein, which down-regulates its own expression and can negatively affect the host cell. The approaches described in this invention effectively circumvent these problems and have allowed for substantial improvements in packaging efficiency.

A number of preferred embodiments of the present invention are summarized below:

1. A method of producing a mammalian cell capable of high efficiency packaging of a recombinant AAV (rAAV) vector, said method comprising the steps of: (a) providing a mammalian cell which comprises a stably integrated AAV cap gene operably linked to a promoter, and a stably integrated AAV rep gene operably linked to a heterologous promoter; (b) replicating the cell of step (a) to produce a population of cells; (c) introducing a helper virus to the population of cells of step (b); and (d) selecting a cell exhibiting helper-virus-inducible rep protein activity.

2. A method according to embodiment 1, wherein said helper virus is an adenovirus.

3. A method according to embodiment 1, wherein said packaging cell is capable of growing at least one half as rapidly as parental-type cells that do not contain an AAV rep gene, and wherein said packaging cell is capable of packaging rAAV vectors to produce at least 100 rAAV particles/cell.

4. A method according to embodiment 1, wherein said mammalian cell of step (a) comprises the combined rep and cap genes of AAV in which the p5 promoter has been replaced by a heterologous promoter.

5. A method according to embodiment 4, wherein said heterologous promoter is a mouse metallothionein I (mMT-I) promoter.

6. A cell produced by the method of embodiment 1, and progeny thereof.

7. A cell produced by the method of embodiment 3, and progeny thereof.

8. A cell produced by the method of embodiment 4, and progeny thereof.

9. A cell produced by the method of embodiment 5, and progeny thereof.

10. A mammalian cell capable of high efficiency packaging of a recombinant AAV (rAAV) vector, said cell comprising a stably integrated cap gene operably linked to a promoter, and a stably integrated rep gene operably linked to a heterologous promoter; wherein said cell exhibits helper-virus-inducible rep protein activity.

11. An AAV packaging cell of embodiment 10, wherein said helper-virus-inducible rep protein activity is inducible by adenovirus.

12. An AAV packaging cell of embodiment 10, wherein said packaging cell is capable of growing at least one half as rapidly as parental-type cells that do not contain an AAV rep gene, and wherein said packaging cell is capable of packaging rAAV vectors to produce at least 100 rAAV particles/cell.

13. An AAV packaging cell of embodiment 10, wherein said cell comprises the combined rep and cap genes of AAV in which the p5 promoter has been replaced by a heterologous promoter.

14. An AAV packaging cell of embodiment 13, wherein said heterologous promoter is a mouse metallothionein I (mMT-I) promoter.

15. An AAV packaging cell of embodiment 10, further comprising a stably integrated recombinant AAV vector, said vector comprising a polynucleotide sequence of interest located between two AAV inverted terminal repeat (ITR) regions.

16. A method of packaging a recombinant AAV vector, comprising the steps of: (a) providing an AAV packaging cell of embodiment 10; (b) introducing a recombinant AAV vector, said vector comprising a polynucleotide sequence of interest located between two AAV inverted terminal repeat (ITR) regions; (c) introducing a helper virus; and (d) incubating the cell under conditions suitable for replication and packaging of AAV.

17. A method of packaging a recombinant AAV vector, comprising the steps of: (a) providing an AAV packaging cell of embodiment 15 which comprises a stably integrated rAAV vector; (b) introducing a helper virus; and (c) incubating the cell under conditions suitable for replication and packaging of AAV.

18. A recombinant AAV vector packaged according to the method of embodiment 16.

19. A recombinant AAV vector packaged according to the method of embodiment 17.

20. A recombinant AAV vector of embodiment 19, wherein said vector comprises a polynucleotide encoding a cystic fibrosis transmembrane conductance regulator (CFTR).

21. A method of determining the relative infectious titer of an rAAV vector preparation, comprising the steps of: (a) introducing a helper virus and serial dilutions of the rAAV vector preparation to AAV packaging cells of embodiment 10; (b) incubating the cells under conditions suitable for replication of AAV; and (c) determining the amount of replicated rAAV vector.

DETAILED DESCRIPTION OF THE INVENTION

Figure 1:
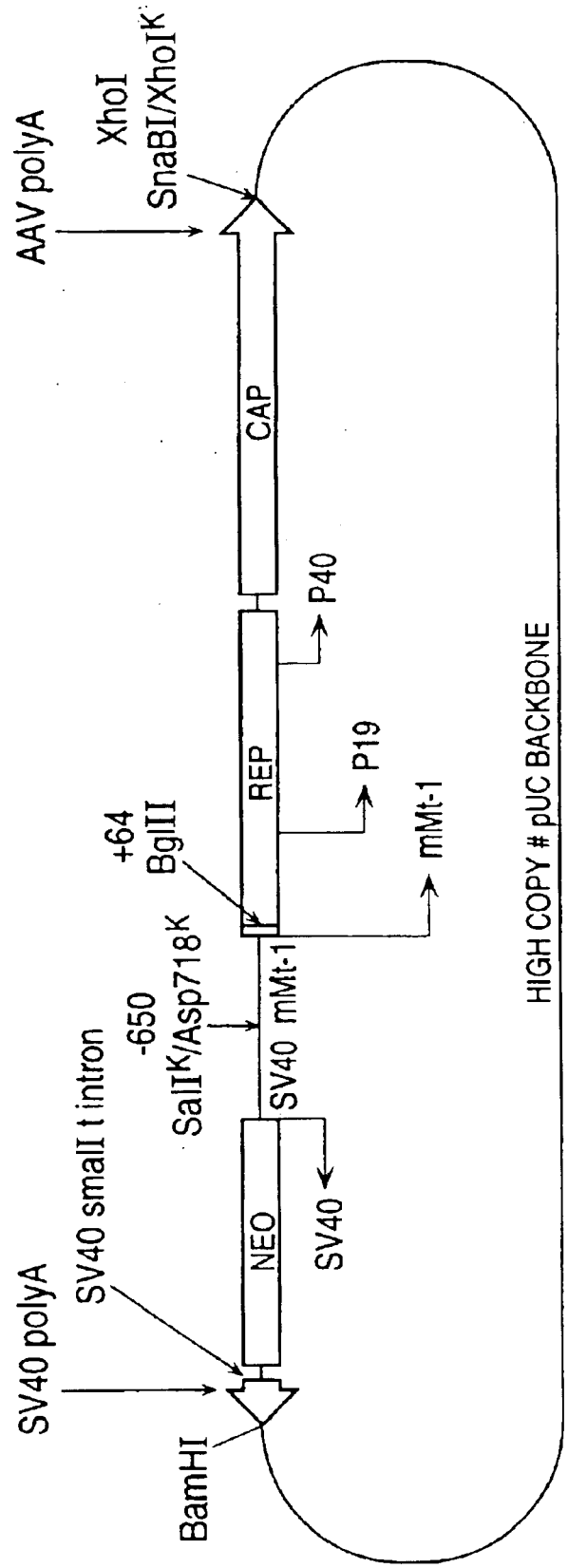
FIG. 1 is a diagram of plasmid pMt-rep/cap//pKO-neo, as described in Example 1.

AAV vectors are recombinant constructs of the AAV virus comprising AAV components necessary for replication and encapsidation, along with a heterologous polynucleotide encoding a protein of interest. These recombinant AAV vectors are potentially powerful tools for human gene therapy, particularly for diseases such as cystic fibrosis and sickle cell anemia. A major advantage of AAV vectors over other approaches to gene therapy is that they do not require ongoing replication of the target cell in order to integrate permanently into the cell's genome.

The invention described herein provides methods and materials for use in the production of high titers of recombinant AAV vectors for use in gene therapy. It also provides methods and materials for determining the relative infectious titer of rAAV preparations.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989), *Oligonucleotide Synthesis* (M. J. Gait Ed., 1984), *Animal Cell Culture* (R. I. Freshney, Ed., 1987), the series *Methods in Enzymology* (Academic Press, Inc.); *Gene Transfer Vectors for Mammalian Cells* (J. M. Miller and M. P. Calos eds. 1987), *Handbook of Experimental Immunology*, (D. M. Weir and C. C. Blackwell, Eds.), Current Protocols in Molecular Biology (F. M. Ausubel, R. Brent, R. E. Kingston, D. D. Moore, J. G. Siedman, J. A. Smith, and K. Struhl, eds., 1987), and Current Protocols in Immunology (J. E. Coligan, A. M. Kruisbeek, D. H. Margulies, E. M. Shevach and W. Strober, eds., 1991). All patents, patent applications, and publications mentioned herein, both supra and infra, are hereby incorporated herein by reference.

Definitions:

The terms "polypeptide", "peptide" and "protein" are used interchangeably to refer to polymers of amino acids of any length. These terms also include proteins that are post-translationally modified through reactions that include glycosylation, acetylation and phosphorylation.

"Polynucleotide" refers to a polymeric form of nucleotides of any length, either ribonucleotides or deoxyribonucleotides, or analogs thereof. This term refers only to the primary structure of the molecule. Thus, double- and single-stranded DNA, as well as double- and single-stranded RNA are included. It also includes modified polynucleotides such as methylated or capped polynucleotides.

"Recombinant," as applied to a polynucleotide, means that the polynucleotide is the product of various combinations of cloning, restriction and/or ligation steps, and other procedures that result in a construct that is distinct from a polynucleotide found in nature.

"Sequence overlap" between two polynucleotides occurs when the nucleotides share a homologous sequence of sufficient length and identity that recombination is facilitated. The level of homology and corresponding frequency of recombination increase with increasing length of the homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination.

A "vector" refers to a recombinant plasmid or virus that comprises a polynucleotide to be delivered into a host cell, either in vitro or in vivo. The polynucleotide to be delivered, sometimes referred to as a "target polynucleotide", may comprise a coding sequence of interest in gene therapy.

A "recombinant AAV vector" (or "rAAV vector") refers to a vector comprising one or more polynucleotides of interest that are flanked by AAV inverted terminal repeat sequences (ITRs). Such rAAV vectors can be replicated and packaged into infectious viral particles when present in a host cell that has been infected with a suitable helper virus and is expressing the AAV rep and cap genes.

AAV "rep" and "cap" genes (encoding replication and encapsidation proteins, respectively) have been found in all AAV serotypes examined, and are described above and in the references cited therein. Typically, the rep and cap genes are found adjacent to each other in the AAV genome, and they are generally conserved among AAV serotypes.

A "helper virus" for AAV refers to a second virus that allows wild-type AAV (which is a "defective" parvovirus) to be replicated and packaged by a host cell. A number of such helper viruses have been identified, including adenoviruses, herpesviruses and poxviruses such as vaccinia.

"Packaging" as used herein refers to a series of subcellular events that results in the assembly and encapsidation of an rAAV vector. Thus, when a suitable vector plasmid is introduced into a packaging cell line under appropriate conditions, it will be assembled into a vector viral particle.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a promoter that is removed from its native coding sequence and operably linked to a different coding sequence is a heterologous promoter.

"Promoter", as used herein, refers to a genomic region that enhances the transcription of a gene or coding sequence to which it is operably linked.

"Operably linked" refers to a juxtaposition, wherein the components so described are in a relationship permitting them to function in their intended manner. A promoter is operably linked to a coding sequence if the promoter promotes transcription of the coding sequence. An operably linked promoter is usually in cis configuration with the coding sequence, but is not necessarily contiguous with it.

"Host cells", "cell lines", "cell cultures", and other such terms denote higher eukaryotic cells, most preferably mammalian cells, which can be used as recipients for recombinant vectors or other transfer polynucleotides, and include the progeny of the original cell that was transduced. It is understood that the progeny of a single cell may not necessarily be completely identical (in morphology or in genomic complement) to the original parent cell.

"Stable integration" of a polynucleotide into a cell means that the polynucleotide has been introduced into a chromosome or mini-chromosome of the cell and, therefore, becomes a relatively permanent part of the cellular genome. Although "episomes" such as plasmids can sometimes be maintained for many generations (particularly if kept under selective pressure), genetic material carried episomally is generally more susceptible to loss than chromosomally-integrated material. Also, the chromatin structure of eukaryotic chromosomes can influence the level of expression of an integrated polynucleotide; and we believe that such effects can sometimes prove beneficial in situations such as those described herein (in which the level of expression of the AAV rep gene can have negative effects upon cellular metabolism). The selection of stable cell lines having properties that are particularly desirable in the context of the present invention, are described in the Detailed Description and Examples below.

"Efficiency" when used in describing a cell line refers to the useful properties of the line; in particular, the growth rate, and (for packaging cell lines) the number of virus particles produced per cell. "High efficiency packaging" indicates production of at least 100 viral particles per cell.

Modes of Carrying Out the Invention:

The method for producing high titers of recombinant AAV vectors comprises several steps. The general strategy involves preparation of mammalian packaging cell lines that comprise a stably integrated AAV cap gene operably linked to promoter, and a stably integrated AAV rep gene operably linked to a heterologous promoter. Packaging cells are then infected or transfected with a plasmid comprising the AAV ITR regions and the target polynucleotide. Under suitable conditions (including suitable growth conditions and infection with a competent helper virus), expression of the rep and cap genes of the packaging cell results in the synthesis of rep and cap proteins which mediate replication and encapsidation of the AAV vector, respectively. Providing a polynucleotide of interest (also referred to as a "target polynucleotide") in-between the AAV ITR sequences of the rAAV vector, thus results in packaging of the target polynucleotide into an infectious rAAV particle which can be used to deliver the polynucleotide to a desired host cell.

By minimizing the extent of sequence overlap between the AAV genes in the packaging cell line and those of the vector plasmid, the proportion of wild-type AAV (i.e., particles not containing the target polynucleotide) can be minimized. As described in the Background section, the presence of contaminating wild-type AAV limits the therapeutic potential of rAAV vector preparations. Besides the lack of sequence overlap in the constructs of the present invention, the p5 promoter region is replaced with a different promoter. The packaging cell lines of the present invention enable the efficient production of rAAV preparations that are of high titer and are substantially free of any contaminating wild-type AAV; attributes that are especially useful in the context of AAV-mediated gene therapy.

Although a first illustration of the principles of the present invention was performed using the AAV2 serotype, it is expected that these same principles will be applicable to other AAV serotypes since it is now known that the various serotypes are quite closely related—both functionally and structurally, even at the genetic level (see, e.g., Blacklow, 1988, pp. 165–174 of "Parvoviruses and Human Disease", J. R. Pattison (ed); and Rose, 1974, Comprehensive Virology 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control.

Producing the Packaging Cell Line:

The parental lines from which packaging cells are generated may be obtained from any cell line that is susceptible to AAV infection, and amenable to culture in vitro. As indicated earlier, AAV has a very broad host range and has been isolated from a variety of mammalian cell types, including simian, human and rodent cells. For human gene therapy, human cell lines in which appropriate helper functions can be expressed are typically preferred. Such human cell lines from which the packaging cell lines may be derived, include, for example, Hela, A549, 293, KB, Detroit, and WI38 cells. We initially selected both Hela cells and A549 cells for demonstrations of the present invention. As described in the Examples below, we were readily able to generate packaging cells from both parental lines tested.

In the case of wild-type AAV (using AAV2 for purposes of illustration), the rep gene is under regulation of the p5 promoter, which is itself strongly down-regulated by rep expression. In constructing packaging cell lines according to the present invention, the cells are provided with a stably integrated AAV cap gene operably linked to a promoter, and a stably integrated AAV rep gene operably linked to a heterologous promoter; as described and illustrated herein. Any heterologous promoter that is not strongly down-regulated by rep gene expression is suitable; but inducible promoters are preferred because constitutive expression of the rep gene can have a negative impact on the host cell. Since the rep and cap genes of the present invention are to be stably integrated into the host cell genome, we believe that location effects (possibly due to chromatin structure) can also influence expression of the genes and can be taken advantage of in obtaining preferred packaging lines. In particular, the methodology described below can be used to generate and select packaging cells that exhibit the desired properties. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase.

An especially preferred sub-class of inducible promoters are those that are induced by the helper virus that is used to complement the replication and packaging of the rAAV vector. A number of helper-virus-inducible promoters are known, including for example, the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

The Examples below illustrate a generally applicable method that can be used to test putative promoters to readily determine whether or not they are helper-virus-inducible and whether or not they will be useful in the generation of high efficiency packaging cells. Briefly, the method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), preferably linked to a positive selectable marker such as an antibiotic resistance gene, are then stably integrated into a suitable host cell (such as the Hela or A549 cells exemplified below). Cells that are able to grow relatively well under selection conditions (e.g. in the presence of the antibiotic) are then tested for their ability to express the rep and cap genes upon addition of a helper virus. As an initial test for rep and/or cap expression, cells can be readily screened using immunofluorescence to detect rep and/or cap proteins (as illustrated in the Examples below). Confirmation of packaging capabilities and efficiencies can then be determined by functional tests for replication and packaging of incoming rAAV vectors (also illustrated below). Using this methodology, we replaced the p5 promoter with a helper-virus-inducible promoter derived from the mouse metallothionein gene, and used the resulting constructs to generate packaging cell lines capable of producing high titers of rAAV particles.

In our system, the AAV cap gene is also stably integrated into the packaging cell line. In a preferred embodiment, the rep and cap genes are introduced into the parental line together, by using a plasmid that contains them both (essentially as they are arranged in the AAV genome, except for replacement of the sequences upstream of rep, i.e. the p5 promoter region). In illustrative examples below, we prepared a plasmid designated pMt-rep/cap//pKO-neo (shown in FIG. 1). The plasmid contains a heterologous promoter linked to a region containing the rep-cap genes. The rest of the rep-cap region, including the p19 promoter and the p40 promoter are retained. The plasmid also contains an AAV polyadenylation signal. Thus, the components of native AAV that are not present in the plasmid include the p5 promoter region (which has been substituted by the heterologous promoter) and the ITRs (which are present in the vector plasmid to be introduced separately).

Cells transfected with rep and cap genes as described above are then selected from untransfected cells according to methods that are routine in the art. Most conveniently, selection is accomplished by linking the rep and cap genes to one or more selectable markers (such as antibiotic resistance genes). For example, in the pMt-ret-rep/cap//pKO-neo construct described below, the neo-resistance gene was included next to the rep-cap sequences. Preferably, such selectable markers are driven by constitutive promoters; and preferably, such markers are introduced in an opposite orientation relative to the AAV rep-cap genes since that tends to reduce the potential for the promoter driving the selectable marker to effect expression of the rep gene (which can be detrimental to the host cell). After transfection and recovery, the cell lines are exposed to the antibiotic for which resistance has been provided (geneticin was used in the case of the constructs referred to above).

Integration into the host cell can be conveniently monitored using Southern analysis, for example. Expression of rep and cap proteins can be assayed using any of a variety of techniques; including structural assays (such as immunofluorescence), and functional assays (such as replication and packaging of an incoming rAAV vector)—both of which are illustrated in the Examples below.

In prior studies, the expression of rep protein in mammalian cells has been correlated with reductions in plating efficiencies and/or decreases in proliferation rates. For example, co-transfection of the rep coding sequence under the control of the metallothionein promoter and pSV2neo into human 293 cells resulted in the generation of neo-resistant cell lines which appeared to progress through DNA synthesis at a slower rate than control cells, even in the absence of heavy-metals (see Yang et al. 1994 *J. Virol.* 68:4847–4856).

Since co-transfection requires the uptake and maintenance of both plasmids, but geneticin only selects for the neo-resistance plasmid, the possibility exists that the rep-containing plasmid may be eventually lost. Moreover, if the introduction of rep exerts a negative effect on the host cell (even when the promoter is not induced), then there would be selective pressure favoring loss of rep activity. Based on those earlier observations, one would expect that cells that maintained and expressed rep would grow slowly. Conversely, cells could predictably resume normal growth rates by losing rep activity.

In our preferred system, the selectable marker is included on the same plasmid as the rep-cap sequences; and both are stably integrated into the host genome. In the case of the plasmid Mt-rep/cap//pKOneo, for example, geneticin-resistant cells would be expected to possess an integrated copy of the neo gene as well as pMt-rep/cap. Since the rep sequences cannot readily be lost in our system, the prior art would predict that the recipient cells would exhibit reduced growth rates.

Surprisingly, when our constructs were introduced into exemplary mammalian host cells (Hela and A549), the rate of proliferation of the geneticin-resistant clones was not significantly affected in either of the cell lines.

Based on the previously observed coupling between rep activity and reduced growth rate, one might expect that the cells exhibiting substantially normal growth rates represented hosts in which the rep gene had somehow become inactivated or lost.

In fact, additional experimentation (described below) indicated that the rep gene had been stably integrated into the resulting cell lines; and, moreover, that introduction of adenovirus into the medium resulted in the synthesis of relatively high levels of functional rep proteins.

These results suggested that our approach could be used to generate stable cell lines that were not subject to the sort of growth limitations observed in the past; and, as described below, subsequent experiments confirmed that these methods could be used to generate cell lines capable of efficiently packaging recombinant AAV vectors.

We have found, using these methods, that one can readily obtain packaging cells that are capable of replicating at least one half as rapidly as the parental cells, and capable of producing more than 100 rAAV particles/cell. In preferred embodiments of the present invention, the cells grow at least two-thirds as rapidly as the parental line, and produce more than 250 rAAV particles/cell. Using two different parental lines to date, we have generated packaging cells that replicate substantially as rapidly as the parent cells (at least about 80% of the rate), and that produce more than about 500 rAAV particles per cell.

Generating rAAV Vectors:

To generate recombinant AAV particles useful for such purposes as gene therapy, the packaging cell line is supplied with a recombinant AAV vector comprising AAV inverted terminal repeat (ITR) regions surrounding one or more polynucleotides of interest (or "target" polynucleotides).

The target polynucleotide is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc.

Preferably, the rAAV vector will also contain a positive selectable marker in order to allow for selection of cells that have been infected by the rAAV vector. Negative selectable markers can also be included; as a means of selecting against those same cells should that become necessary or desirable. In a preferred embodiment, one can make use of the "bifunctional selectable fusion genes" described by S. D. Lupton; see, e.g., PCT/US91/08442 and PCT/US94/05601. Briefly, those constructs involve direct translational fusions between a dominant positive selectable marker a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

By way of illustration, we have used rAAV vectors containing polynucleotides that encode a functional cystic fibrosis transmembrane conductance regulator polypeptide (CFTR) operably linked to a promoter. As is now known in the art, there are a variety of CFTR polypeptides that are capable of reconstructing CFTR functional deficiencies in cells derived from cystic fibrosis patients. For example, Rich et al. (1991, Science, 253: 205–207) described a CFTR derivative missing amino acid residues 708–835, that was capable of transporting chloride and capable of correcting a naturally occurring CFTR defect. Egan et al. (1993) described another CFTR derivative (comprising about 25 amino acids from an unrelated protein followed by the sequence of native CFTR beginning at residue 119) that was also capable of restoring electrophysiological characteristics of normal CFTR. To take two additional examples, Arispe et al. (1992, Proc. Natl. Acad. Sci. USA 89: 1539–1543) showed that a CFTR fragment comprising residues 433–586 was sufficient to reconstitute a correct chloride channel in lipid bilayers; and Sheppard et al. (1994, Cell 76: 1091–1098) showed that a CFTR polypeptide truncated at residue 836 to about half its length was still capable of building a regulated chloride channel. Thus, the native CFTR protein, and mutants and fragments thereof, all constitute CFTR polypeptides that are useful under this invention.

Other useful target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with some lung and breast cancers.

Since the therapeutic specificity of the resulting recombinant AAV vector is determined by the plasmid introduced, the same packaging cell line can be used for any of these applications. The plasmid comprising the specific target polynucleotide is introduced into the packaging cell for production of the AAV vector by one of several possible methods; including, for example, electroporation.

Helper virus can be introduced before, during or after introduction of the rAAV vector. As illustrated in Example 10, the plasmid can be co-infected into the culture along with the helper virus. The cells are then cultured for a suitable period, typically 2–5 days, in conditions suitable for replication and packaging as known in the art (see references above and examples below). Lysates are prepared, and the recombinant AAV vector particles are purified by techniques known in the art.

In a preferred embodiment, also illustrated in the Examples below, the recombinant AAV vector is itself stably integrated into a clone of the packaging cell line. Such a stable, vector-containing packaging line can be grown and stored until ready for use. To induce production of rAAV particles, the user simply infects the cells with helper virus and cultures the cells under conditions suitable for replication and packaging of AAV (as described below).

Using the Cell Lines for Assaying AAV Titer:

We have also used the packaging cell lines of the present invention to set up an rAAV infectious titer assay.

In particular, as described below, we have demonstrated that there is a linear relationship between incoming rAAV and replicated rAAV over a range of greater than two logs.

Thus, in another embodiment of this invention, we provide a method for determining the relative infectious titer of an rAAV preparation. Although the amount of helper virus and the incubation time influence the amount of rep activity, they can be readily optimized and kept constant, as illustrated below. To conduct the assay, aliquots of the packaging cell line are introduced with a standard amount of helper virus and serial dilutions of the rAAV preparation to be tested. The relative infectious titer of the AAV is indicated by the amount of replicated AAV present in each aliquot after suitable incubation; and can be compared to a preparation of known titer.

The examples presented below are provided as a further guide to the practitioner of ordinary skill in the art, and are not to be construed as limiting the invention in any way.

EXAMPLES

Example 1

Construction of a Plasmid Encoding the Rep-Cap Sequences Operably Linked to a Heterologous Promoter As a first illustration, we constructed a plasmid containing the wild type rep and cap genes (from deoxyribonucleotide 311 to 4493 of the AAV genome); operably linked to the mouse metallothionein I (mMt-I) gene promoter (from −650 to +64 relative to the start of transcription; as described by Srivastava et al. 1983. *J. Virol.* 45:555–564; and Hamer and Walling (1992) *J. Mol. Appl. Genet.* 1:273–288).

This construction effectively removes both ITR's and substitutes the mMt-I promoter for the p5 promoter while maintaining all of the AAV reading frames, the p19 and p40 promoters and the polyadenylation signal. Also included within this vector is pKOneo, which contains the neo gene (providing resistance to neomycin and gentamicin) under control of the SV40 early promoter; as well as SV40 small t intron and SV40 polyadenylation signal oriented in the opposite transcriptional direction relative to pMt-rep/cap (Ito et al. 1994 *Cancer Lett.* 76:33–39).

Standard procedures were followed for plasmid construction, growth and purification (Ausubel et al. (ed.) 1987. *Current Protocols in Molecular Biology*, Greene Publishing Associates, Brooklyn, N.Y.).

The resulting plasmid, designated pMt-rep/cap//pKO-neo, is shown in FIG. 1.

Example 2

Integration of the Rep-Cap Genes into Mammalian Cell Lines

We introduced plasmid pMt-rep/cap//pKO-neo into exemplary mammalian cell lines in order to examine expression of the rep and cap genes after integration into the host cell genome.

Human Hela and A549 [American Type Culture Collection (ATCC®)] cells were grown in Dulbecco's modified Eagle's medium (DMEM) supplemented with antibiotics and 10% fetal bovine serum. All DNA transfections were carried out by electroporation of 15—30 $\mu$g pMT-rep/cap//pKO-neo plasmid into 4 ×10$^6$ cells in 800 $\mu$l serum-free medium in a 0.4 cm cuvette at 250 volts/960 $\mu$F using a Gene Pulser (Bio-Rad).

After electroporation, the cells were plated at low density in the presence of 1 mg/ml active component geneticin (Gibco-BRL). Individual colonies were ring cloned, expanded and maintained in 1 mg/ml geneticin.

In prior studies, the expression of rep protein in mammalian cells has been correlated with reductions in plating efficiencies and/or decreases in proliferation rates. For example, co-transfection of the rep coding sequence under the control of the metallothionein promoter and pSV2neo into human 293 cells resulted in the generation of neo-resistant cell lines which appeared to progress through DNA synthesis at a slower rate than control cells, even in the absence of heavy-metals (see Yang et al. 1994 *J. Virol.* 68:4847–4856).

Since co-transfection requires the uptake and maintenance of both plasmids, but geneticin only selects for the neo-resistance plasmid, the possibility exists that the rep-containing plasmid may be eventually lost. Moreover, if the introduction of rep exerts a negative effect on the host cell (even when the promoter is not induced), then there would be selective pressure favoring loss of rep activity. Based on those earlier observations, one would expect that cells that maintained and expressed rep would grow slowly. Conversely, cells could predictably resume normal growth rates by losing rep activity.

In our preferred system, the selectable marker is included on the same plasmid as the rep-cap sequences; and both are stably integrated into the host genome. In the case of the plasmid Mt-rep/cap//pKOneo, for example, geneticin-resistant cells would be expected to possess an integrated copy of the neo gene as well as pMt-rep/cap. Since the rep sequences cannot readily be lost in our system, the prior art would predict that the recipient cells would exhibit reduced growth rates.

Surprisingly, when our constructs were introduced into exemplary mammalian host cells (Hela and A549), the rate of proliferation of the geneticin-resistant clones was not significantly affected in either of the cell lines.

Based on the previously observed coupling between rep activity and reduced growth rate, one might expect that the cells exhibiting substantially normal growth rates represented hosts in which the rep gene had somehow become inactivated or lost.

In fact, additional experimentation (described below) indicated that the rep gene had been stably integrated into the resulting cell lines; and, moreover, that introduction of adenovirus into the medium resulted in the synthesis of relatively high levels of functional rep proteins.

These results suggested that our approach could be used to generate stable cell lines that were not subject to the sort of growth limitations observed in the past; and, as described below, subsequent experiments confirmed that these methods could be used to generate cell lines capable of efficiently packaging recombinant AAV vectors.

By combining the methodology described herein with the teachings and materials available in the art, one of ordinary skill in the field will readily be able to prepare embodiments of the present invention such as those illustrated in these Examples. For convenience, however, we are depositing an exemplary plasmid (pMT-rep/cap//pKo-neo), as well as exemplary packaging cells (Hela clone 37 and A549 cline 20) (all as described in these Examples) with the American Type Culture Collection, P.O. Box 1549 Manassas, Va. 20108, having the following three Accession Numbers (97049, CRL-1 1831, and CRL-1 1877, respectively). The deposits were made under the terms of the Budapest Treaty and are incorporated herein by reference. Upon allowance and issuance of this application as a United States Patent, all restrictions on availability of the deposit will be irrevocably removed; and access to the designated deposits will be available during pendency of the above-named application to one determined by the Commission to be entitled thereto under 37 CFR 1.14 and 35 USC 1.22. Moreover, the designated deposits will be maintained for a period of thirty years from the date of deposit, or for five years after the last request for the deposit; or for the enforceable life of the U.S. patent, whichever is longer. The deposited materials mentioned herein are intended for convenience only, and are not required to practice the present invention in view of the descriptions herein; and in addition these materials are incorporated herein by reference.

Example 3

Detection of Rep Protein by Indirect Immunofluorescence

We examined rep protein expression in the transfected cell lines (exemplary clones derived from Hela or A549 cells) using indirect immunofluorescence (IF).

Transfected and control cells were seeded (at $1.6 \times 10^4$ cells/chamber) onto Lab-Tek 8 well chamber slides (Nunc Inc., Ill.) in 200 μl culture medium and incubated overnight. The cells were then treated individually or in combination with wild type AAV (MOI=5), adenovirus (MOI=10) and ZnSO4 (100 μM) for ~30 hours. After removing the culture medium, the cells were washed three times with phosphate buffered saline (PBS) at 0° C. and fixed for 1–2 min. with acetone. The cells were then washed three additional times with PBS and incubated overnight with "WT" medium (1% nonfat dry milk, 0.5 mg/ml bovine serum albumin, 150 mM NaCl, 50 mM HEPES (pH 7.5), 0.1% Tween 20 and 1 mM $NaN_3$).

Anti-rep antibody (rabbit anti-Rep78.93; Trempe et al. 1987 *Virology* 161:18–28) was diluted 1:250 in WT and 100 μl added to each well for 1 hour at room temperature (RT). The cells were washed five times with WT and then incubated with 100 μl of a 1:100 dilution of anti-rabbit IgG FITC conjugate secondary antibody (Sigma Chemical Corp.) in the dark for 1 hour at RT. The cells were then washed three times with WT and two times with PBS in the dark and examined with an Axioskop H fluorescence microscope (Zeiss, Germany).

When adenovirus was included in the culture medium, rep protein was detectable in a number of the cells examined (8 out of 23 A549 clones and 3 out of 28 Hela clones). The addition of heavy metals did not significantly affect the observed rep expression under any conditions.

These observations suggest that very little, if any, rep protein is synthesized in these cells in the absence of an adenovirus infection. Southern analysis of genomic DNA isolated from a subset of the rep (IF) positive cells hybridized with a labeled cap probe demonstrated that a single copy of the rep-cap sequences was integrated into the cellular DNA.

Although not wishing to be bound by theory regarding the mechanism by which the metallothionein promoter is helper-virus-inducible, our results suggest that it may contain an adeno-responsive element, which would be consistent with an observation made by Carthew et al., 1985, Cell 43:439–448. In any case, the method we describe for obtaining and testing a helper-virus-inducible promoter is a general one that can be readily applied to any promoter of potential interest by simply swapping it into rep constructs and screening for colonies as we describe herein.

In subsequent experiments, exemplary clones (of Hela and A549 origin) were tested for their ability to replicate recombinant AAV genomes after infection, as described below.

Example 4

Replication Activity of IF+ Cells

We examined whether the pMt-rep/cap//pKO-neo transfected cell lines exhibited functional replication activity. We selected a recombinant AAV preparation including the cystic fibrosis cDNA (AAVCFTR) (Riordan et al. 1989 *Science* 245:1066–1073) as an exemplary recombinant AAV. Serial dilutions of the rAAV preparation were incubated +/− adenovirus (MOI=25) on rep IF+ cells (Hela clone 37 and A549 clone 20). AAVCFTR virus was diluted from $1.2 \times 10^8$ to $1.2 \times 10^3$ particles (as determined by slot blot) and incubated on both cell lines ($2.5 \times 10^5$ cells/well in a 6 well dish) for 48 hours +/− adenovirus (MOI=25 pfu/cell). In order to control for the effect of adenovirus infection on the cells infected with the virus, the culture medium from each well was removed to a labeled tube and any cells still attached to the culture dish were trypsinized and pooled with cells present in the media. The cell suspension was centrifuged at 3000 rpm for 5 min., after which the supernatant was removed and total nucleic acid was prepared from the cell pellet (according to Ausubel et al. (ed.) 1987 *Current Protocols in Molecular Biology* Greene Publishing Associates, Brooklyn, N.Y.).

Negative controls for the experiment included the incubation of $1.2 \times 10^8$ AAVCFTR particles on either cell line without adenovirus.

Fifteen micrograms of nucleic acid for each sample, as well as untreated Hela clone 37 DNA +/−20 pg of AAVCFTR plasmid (positive control for Southern), was digested with EcoRI, subjected to gel electrophoresis, transferred to nitrocellulose and probed with a 1.488 kb EcoRI fragment from within the CFTR cDNA. Lanes 15–18 (FIG. 2) contain parental Hela and A549 genomic DNA +/−20 pg AAVCFTR plasmid to show the hybridization pattern of the endogenous human CFTR gene (Rommens et al. 1989 *Science* 245:1059–1065) and the 1.488 kb CFTR cDNA signal, respectively. A hybridization signal migrating at 1.488 kb is present in DNA isolated from both the Hela clone 37 and A549 clone 20 cell lines after infection by AAVCFTR virus and adenovirus (FIG. 2, lanes 1, 2 and 8).

Figure 2:
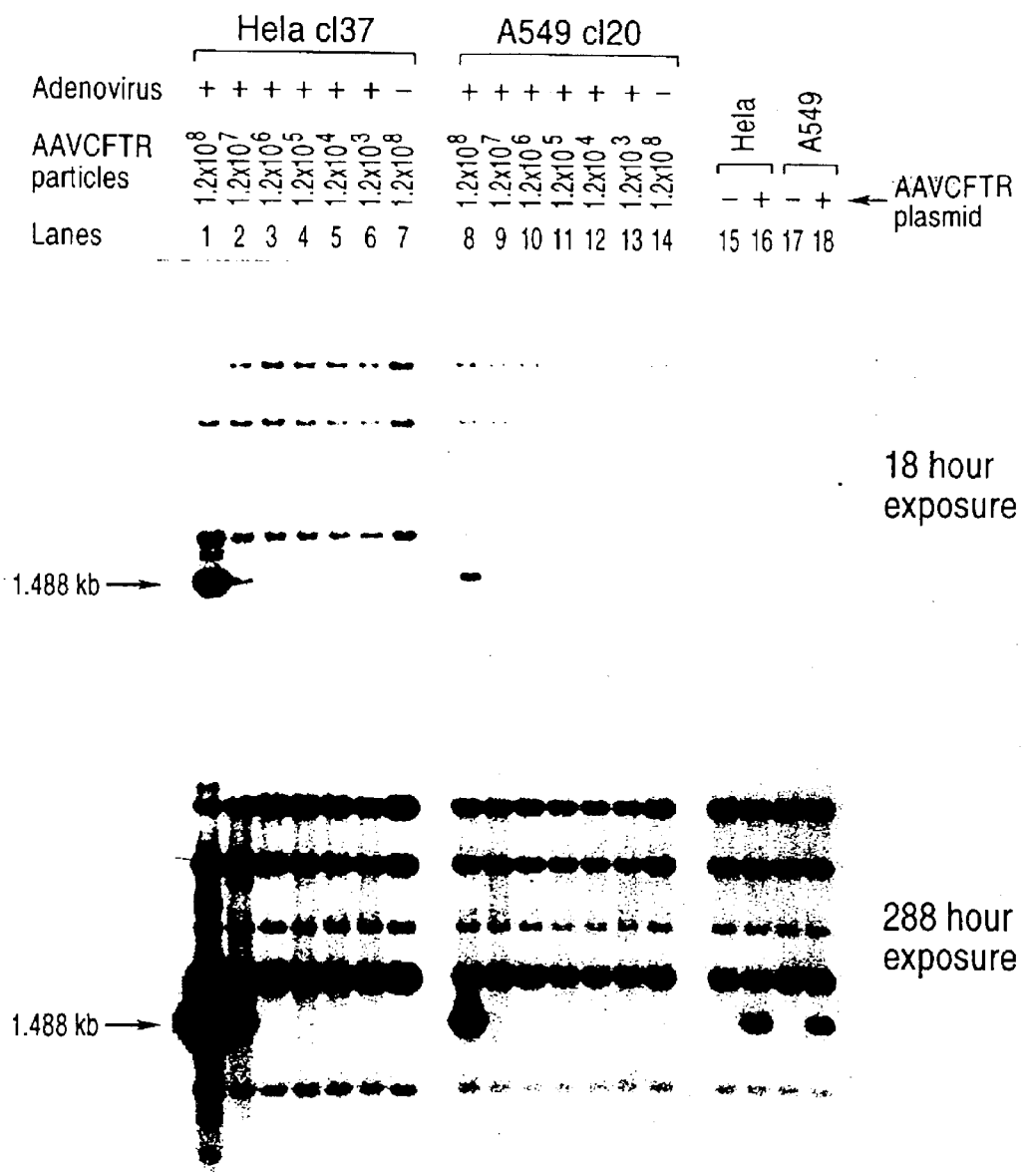
FIG. 2 is a reproduction of Southern blots demonstrating that packaging cells produced according to the present invention have sufficient rep activity to replicate an incoming rAAV vector, as described in Example 4.

These results demonstrated that both Hela clone 37 and the A549 clone 20 lines possessed sufficient rep activity to replicate the incoming AAVCFTR DNA upon infection, although both lines absolutely required adenovirus (FIG. 2, compare lanes 1 and 7 or 8 and 14).

Example 5 rAAV Infectious Titer Assays

Additional rep activity assays were performed in order to determine whether there was a linear relationship between incoming AAVCFTR virus and replicated AAVCFTR sequences (which could be exploited as the basis of an rAAV infectious titer assay).

Figure 3:
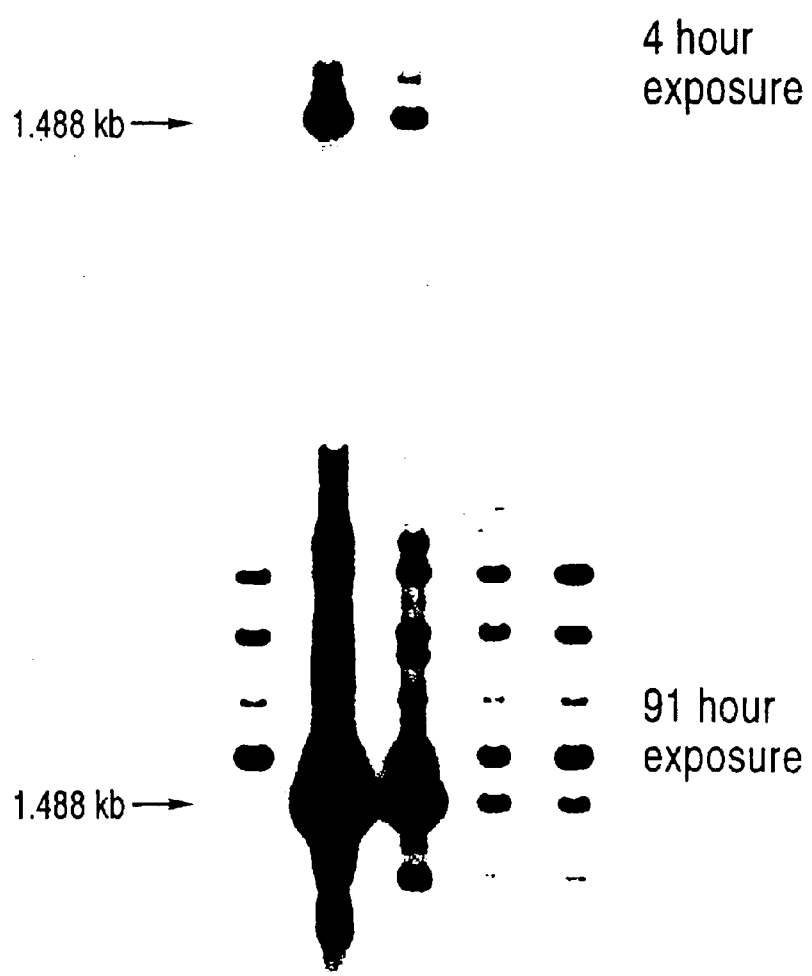
FIG. 3 is a reproduction of Southern blots demonstrating that packaging cells produced according to the present invention are capable of replicating an AAV genome in the presence of adenovirus, and that this activity can be used to quantify the number of infectious viral particles present in a given sample, as described in Example 5.

Three log dilutions from $1.2 \times 10^9$ to $1.2 \times 10^7$ AAVCFTR particles, as determined by slot blot hybridization, were cultured in 2.5 ml media on $2.5 \times 10^5$ Hela clone 37 cells plus adenovirus (MOI=25 pfu/cell) for 48 hours in a 6 well culture dish. As a negative control, $1.2 \times 10^9$ AAVCFTR particles minus adenovirus was included. After 48 hours, total nucleic acid was prepared from the cells for Southern analysis to detect replicated CFTR sequences, as previously described (FIG. 3). Hela clone 37 cells cultured in the presence of $1.2 \times 10^9$ AAVCFTR particles only (FIG. 3, lane 1) displayed a hybridization pattern reflecting the genomic organization of the endogenous human CFTR gene. The addition of 20 pg of AAVCFTR plasmid into Hela clone 37 DNA shows where the 1.488 kb EcoRI fragment migrates on this blot (FIG. 3, lane 5). The samples from the serial dilutions of AAVCFTR virus plus adenovirus are shown in lanes 2–4, respectively (FIG. 3). The hybridization observed at 1.488 kb appears to be proportional to the input AAVCFTR virus and absolutely dependent on the presence of adenovirus (compare lanes 1 and 2).

These results demonstrate that packaging cells produced according to the present invention are capable of replicating an AAV genome in the presence of adenovirus, and that this activity can be used to quantify the number of infectious viral particles present in a given sample. In this particular assay, the linear response required at least $1.2 \times 10^7$ AAVCFTR particles cultured on $2.5 \times 10^5$ Hela clone 37 cells ($\geq$MOI=48 particles/cell). The particle number was determined by slot blot hybridization of the AAVCFTR virus preparation and may reflect the contribution of infectious and defective AAVCFTR particles; whereas the infectious assay described above should only detect infectious particles.

Example 6

AAVCFTR Plasmid DNA Gene Transfer into Packaging Cells

Figure 4:
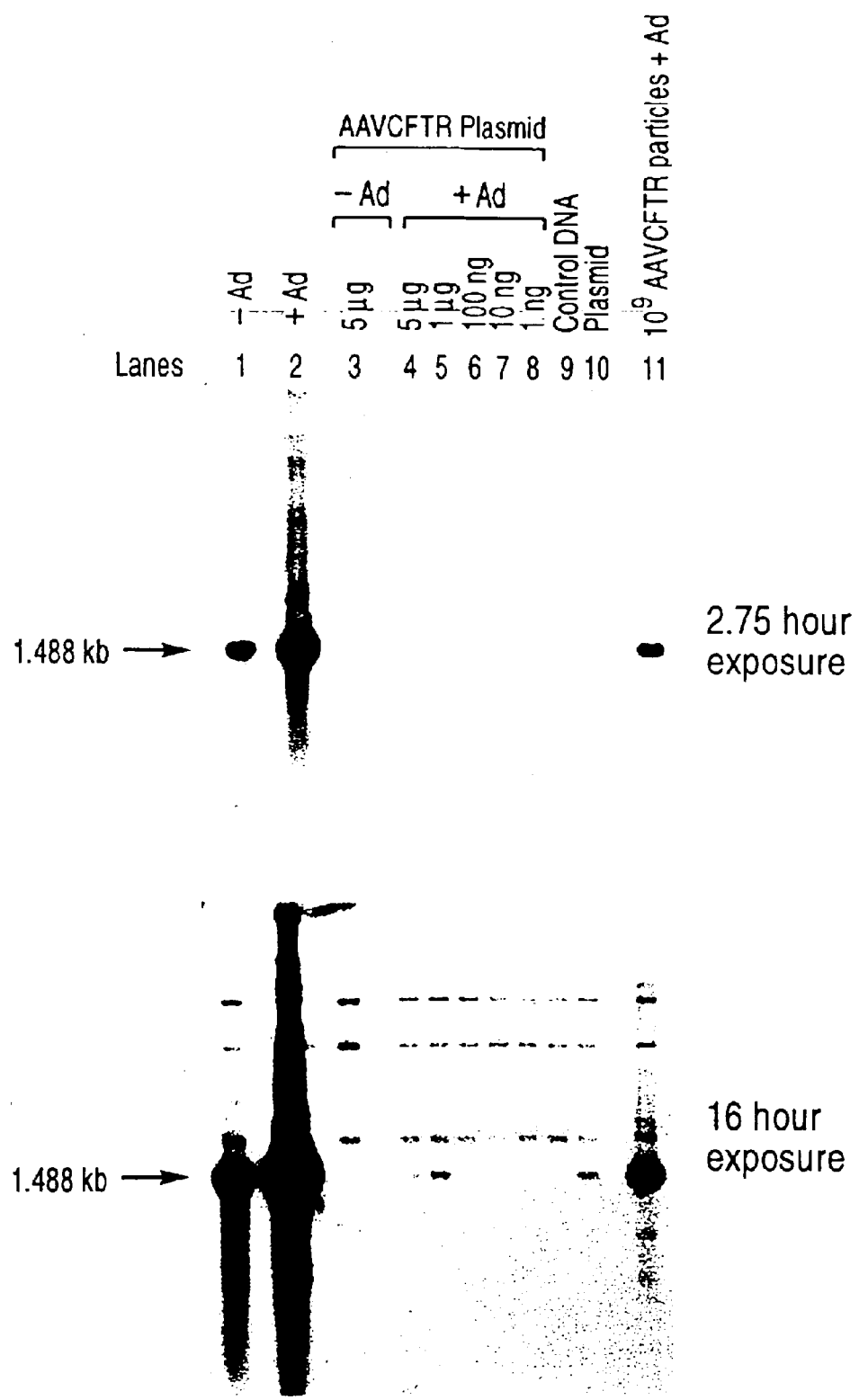
FIG. 4 is a reproduction of Southern blots demonstrating that packaging cells produced according to the present invention express rep protein and are able to replicate recombinant AAV plasmid DNA genomes introduced by transfection, as described in Example 6.

Current methods for the production of recombinant AAV (rAAV) virus include the transient transfection of plasmid vectors containing the rAAV sequences. One or more steps are undertaken to remove the plasmid DNA from a rAAV preparation. AAVCFTR plasmid DNA was incubated directly onto packaging cells (Hela clone 37) +/− adenovirus to determine whether the above-described infection assay would detect non-viral DNA. As a control, AAVCFTR plasmid (10 µg) was electroporated as previously described into $4\times10^6$ Hela clone 37 cells and then transferred to a 100 mm culture dish. The following day, the cells were washed in phosphate buffered saline (PBS), trypsinized and $2.5\times10^5$ cells seeded in duplicate in a 6-well dish +/− adenovirus (MOI=25 pfu/cell). Seven additional wells were seeded with $2.5\times10^5$ Hela clone 37 cells each and cultured with a dilution series of AAVCFTR plasmid +/− adenovirus (MOI=25 pfu/cell) or AAVCFTR virus ($1\times10^9$ particles) plus adenovirus. Total nucleic acid was prepared 48 hours post-infection and Southern analysis was performed as previously described. Lanes 9 and 10 (FIG. 4) show the hybridization pattern of the endogenous CFTR gene and the migration of CFTR cDNA (20 pg) spiked into human genomic DNA when digested with EcoRI and probed with the 1.488 kb CFTR cDNA fragment. Electroporation of the AAVCFTR plasmid into Hela clone 37 cells resulted in a signal migrating at 1.488 kb (FIG. 4, lane 1) and represents the amount of AAVCFTR plasmid present in these cells 24 hours after transfection. An equal number of electroporated cells incubated with adenovirus reveals significantly more signal migrating at 1.488 kb reflecting the ability of Hela clone 37 cells to amplify the AAVCFTR plasmid genome after electroporation (FIG. 4, lane 2). Lanes 3 and 4 show the result of incubating 5 µg AAVCFTR plasmid (+/− adenovirus, respectively) directly onto Hela clone 37 cells without transfection. Although there is a small amount of hybridization which is amplified in the presence of adenovirus, the signal is significantly lower than that derived from either AAVCFTR plasmid transfection (FIG. 4, lane 2) or AAVCFTR virus infection (FIG. 4, lane 11,). Lanes 5–8 show the results of incubating 1 µg, 100 ng, 10 ng and 1 ng AAVCFTR plasmid, respectively, on Hela clone 37 cells in the presence of adenovirus.

These results demonstrate that, in the presence of adenovirus infection, the packaging cells produced according to the present invention express rep protein and are able to replicate recombinant AAV plasmid DNA genomes introduced by transfection. This activity was dependent upon the transfection of AAV plasmid DNA into the packaging cells (e.g. co-incubation of plasmid DNA containing AAV sequences and adenoviral infection did not result in significant replication of the input plasmid).

Example 7

Time Course of rAAV Infectious Titer Assay

A time course examining the replication of AAVCFTR virus after infection of packaging cells in the presence of adenovirus was performed to verify that the time of viral incubation was not influencing the rAAV infectious assay described above.

Figure 5:
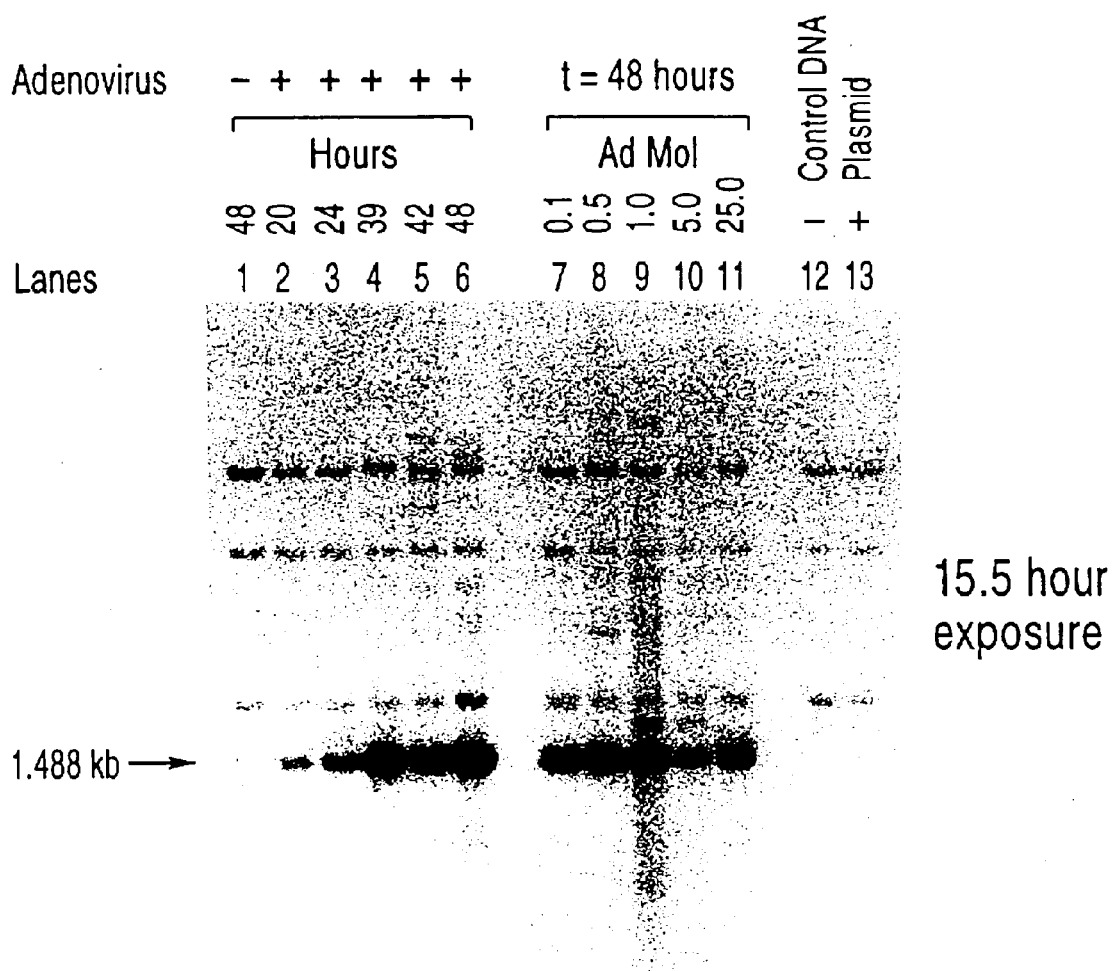
FIG. 5 is a reproduction of Southern blots demonstrating that the infectious rAAV titering assay described in Example 5 had proceeded for a sufficient amount of time to reach a maximum, as described in Example 7.

To determine the time course of AAVCFTR virus replication, $1.5\times10^5$ Hela clone 37 cells were cultured with $1.2\times10^9$ AAVCFTR particles and adenovirus (MOI=5 pfu/cell) in a 6-well dish and harvested at various times after infection for Southern analysis. Control human DNA +/− spiked AAVCFTR plasmid (20 pg) was also included in the Southern as a control (FIG. 5, lanes 12, 13). Lanes 2–6 show the result of harvesting total nucleic acid at 20, 24, 39, 42 and 48 hours post-infection (FIG. 5). The signal observed at 1.488 kb increases to a maximum by 39 hours (FIG. 5, lane 4) and a comparison of lanes 1 and 6 demonstrates the dependence of this assay on input adenovirus.

These results demonstrate that the infectious rAAV titering assay described in Example 5 had proceeded for a sufficient amount of time to reach a maximum.

Example 8

Adenovirus Titration of rAAV Infectious Titer Assay

The effect of adenovirus MOI on the rAAV infectious titer assay was performed to confirm that adenovirus was not limiting in the assay.

The dilution of input adenovirus from MOI=25.0 to 0.1 cultured with $1.2\times10^9$ AAVCFTR particles on $2.5\times10^5$ Hela clone 37 cells and harvested at 48 hours did not reduce the signal intensity migrating at 1.488 kb (FIG. 5, lanes 7–11).

These data, taken together, show that neither the time of incubation nor the amount of added adenovirus significantly impacts the initial titering results presented in Examples 4 and 5.

Example 9

Production of Infectious AAVCFTR Virions After Transfection

We then demonstrated that the AAVCFTR plasmid, introduced into packaging cells of the present invention, could be effectively packaged into infectious AAVCFTR virions.

In particular, AAVCFTR plasmid (10 µg) was electroporated as previously described into $2\times10^6$ exemplary packaging cells (Hela clone 37) and plated onto a 100 mm culture dish. The following day the cells were washed with PBS, trypsinized, pelleted and brought up in culture media. The cells were counted and $2\times10^5$ seeded into two wells of a 6-well culture dish. The cells were incubated with 2.5 ml culture-media +/− adenovirus (MOI=10). After 48 hours, the cells were scraped into the media and subjected to 3 freeze/thaw cycles in dry ice/EtOH bath and 37° C. H$_2$O bath, respectively. After centrifugation at 3000 rpm for 10 min., the supernatant was removed (~2.5 ml) for titering and total nucleic acid was isolated from the post freeze/thaw cell debris pellets to look for rAAVCFTR replicative intermediates. The supernatant from the electroporated packaging cells plus adenovirus (50 and 500 µl) and one dilution (500 µl) of the non-adenovirus infected control were cultured in a 2.5 ml final volume for 48 hours in the presence of additional adenovirus (MOI=5) for titering as described in Examples 4 and 5. No steps were undertaken to remove potential plasmid contamination from the electroporation or adenovirus from the initial cultures to generate additional rAAVCFTR virions.

Figure 6:
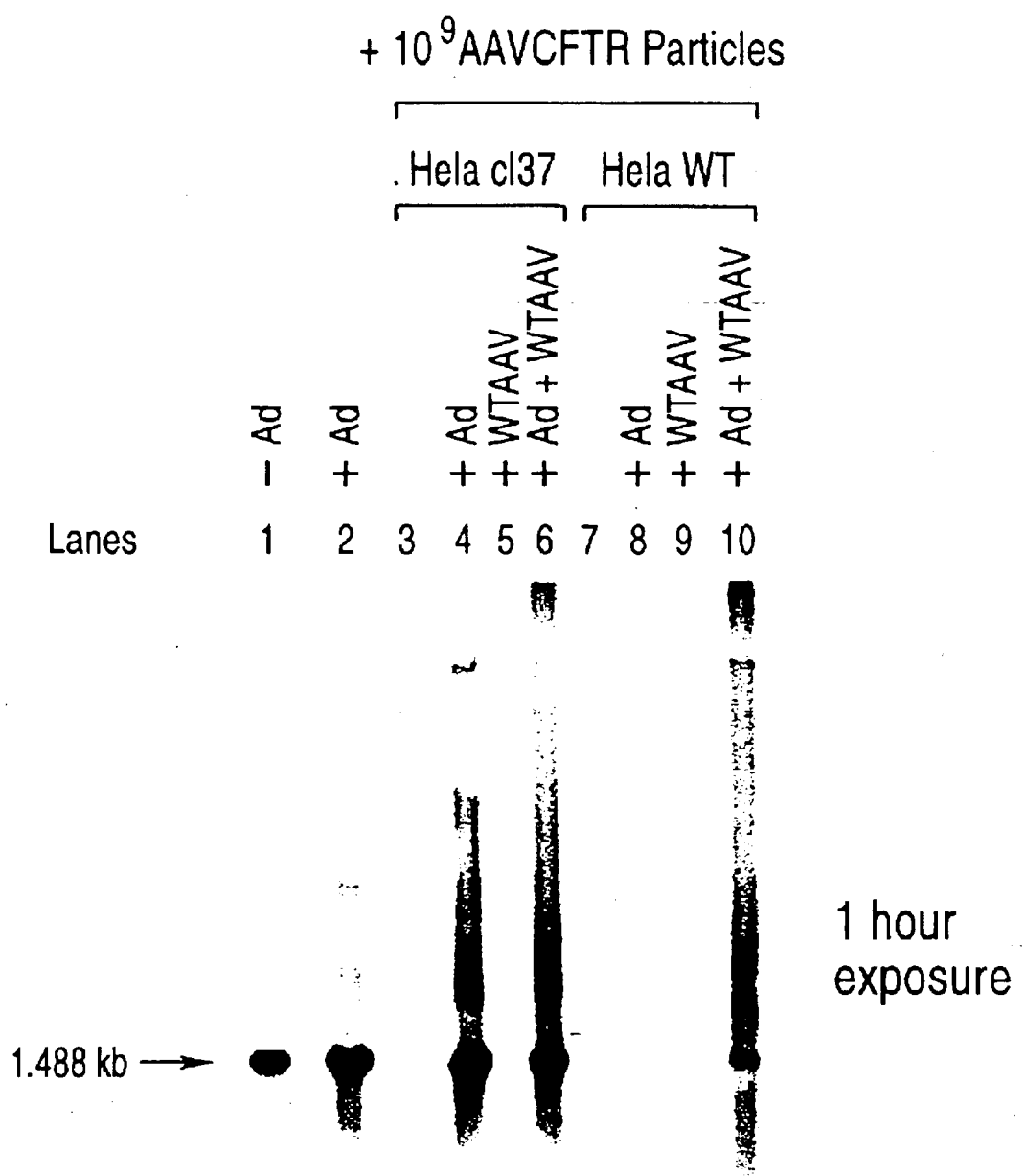
FIGS. 6 and 7 are reproductions of Southern blots demonstrating that packaging cells produced according to the present invention can replicate and package rAAV vector genomes into infectious virions by either transfection or infection, as described in Examples 9 and 10.

Southern analysis of nucleic acid isolated from the post freeze/thaw cell pellets, digested with EcoRI and probed for CFTR sequences is shown in FIG. 6. As described previously in FIG. 4, AAVCFTR plasmid can be detected in Hela clone 37 cells after electroporation, and the hybridization signal migrating at 1.488 kb increases after infection with adenovirus (FIG. 6, lanes 1 and 2).

Figure 7:
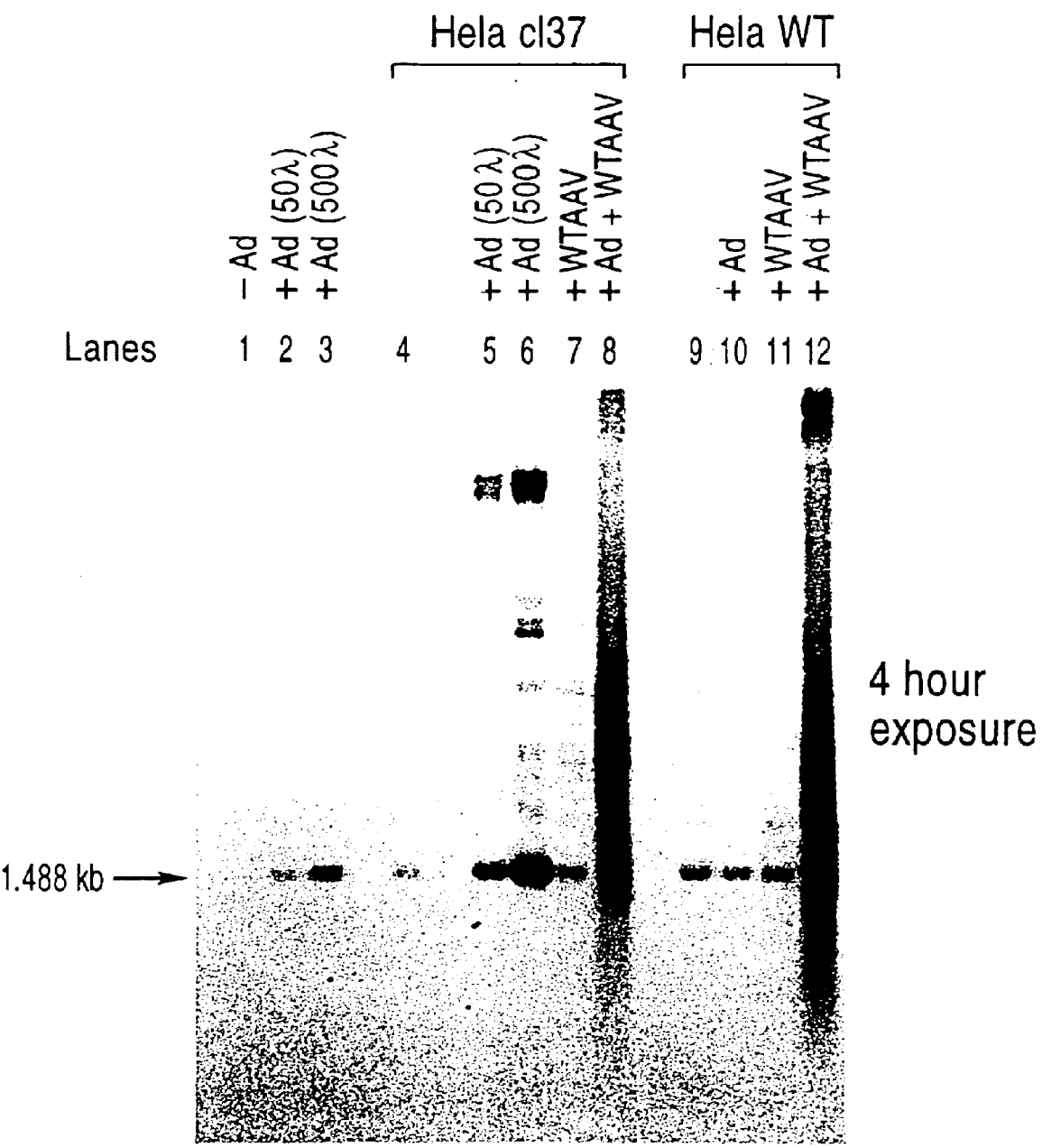

The titering of supernatants derived from Hela clone 37 cells electroporated with AAVCFTR plasmid +/− adenovirus is presented in FIG. 7, lanes 1–3. A slight signal migrating at 1.488 kb can be detected in DNA isolated from Hela clone 37 cells incubated with supernatant derived from the minus adenovirus control and reflects a small amount of contaminating input AAVCFTR plasmid from the electroporation (FIG. 7, lane 1). Supernatant derived from a duplicate well cultured with adenovirus and titered on Hela clone 37 cells revealed significantly more hybridization migrating at 1.488 kb relative to control conditions (FIG. 7, compare lanes 3 and 1).

These results demonstrate that after transfection of packaging cells with a recombinant AAV plasmid and infection with adenovirus, the rAAV sequences were replicated and assembled into infectious rAAV virions.

Example 10

Production of Infectious Recombinant AAV Virions After Infection with rAAV Virus We further examined the ability of the packaging cells to generate infectious rAAV virions after infection. Several control experiments were included to determine whether newly synthesized virus was generated. These include the use of parental Hela cells and conditions which should not allow for the generation of rAAV. Both Hela clone 37 and parental Hela cells ($2.5 \times 10^5$) were seeded onto 6-well dishes and incubated for 48 hours under the following conditions: plus $10^9$ AAVCFTR particles alone; plus $10_9$ AAVCFTR particles with either adenovirus (MOI=10) or wild type AAV (MOI=5); or all three. After 48 hours, the cells were harvested as described in Example 9. Nucleic acid was isolated from the post freeze/thaw cell pellets for Southern analysis and the supernatants titered.

Southern analysis of nucleic acid isolated from either Hela clone 37 cells (lanes 3–6) or parental Hela cells (lanes 7–10) treated under the conditions described above is presented in FIG. 6. Treatment of either cell line with $10^9$ AAVCFTR particles alone did not result in the generation of replicated AAVCFTR sequences (FIG. 6, lanes 3 and 7, respectively). The addition of adenovirus to Hela clone 37 cells, but not to parental Hela cells, resulted in the generation of a significant amount of signal migrating at 1.488 kb, consistent with previous observations (FIG. 6, lanes 4 and 8). Wild-type AAV did not result in the generation of replicated AAVCFTR in either cell line, due to the lack of adenovirus helper function (FIG. 6, lanes 5 and 9). Finally, the co-infection of $10^9$ AAVCFTR particles with both adenovirus and wild type AAV results in the generation of replicated AAVCFTR sequences in both Hela clone 37 and parental Hela cells (FIG. 6, lanes 6 and 10). The signal migrating at 1.488 kb may be reduced in the Hela clone 37 cells and the overall lane background is increased due to competition between the wild type and recombinant AAVCFTR virus replication.

The supernatants generated after freeze/thawing were incubated on fresh Hela clone 37 cells (500 µl diluted to 2.5 ml unless otherwise indicated) in the presence of adenovirus (MOI=5) for titering. No steps were undertaken to remove input AAVCFTR virus, wild type AAV or adenovirus from the initial cultures to generate additional rAAVCFTR virions. After 48 hours, total nucleic acid was prepared and Southern analysis performed as previously described for the detection of AAVCFTR replication.

The result of culturing both Hela clone 37 and parental Hela cells with $10^9$ AAVCFTR particles under various conditions is presented in FIG. 7, lanes 4–12. All lanes reveal the presence of rAAVCFTR virus in the supernatants which is due to the fact that no attempt was made to purify de novo generated virions from input virus. Any signal above the input signal should correlate with conditions that resulted in the amplification of AAVCFTR signal observed in FIG. 6. These conditions include: $10^9$ AAVCFTR particles plus adenovirus and/or wild type AAV in parental Hela cells (FIG. 6, lanes 4, 6 and 10). All other conditions did not result in the replication of AAVCFTR sequences and should display a similar signal after titering, reflecting the presence of input AAVCFTR virus (FIG. 7; lanes 4, 7, 9–11).

As expected, co-incubation of AAVCFTR, adenovirus and wild type AAV resulted in the generation of de novo AAVCFTR virus production in both Hela clone 37 and parental Hela cells (FIG. 7; lanes 8 and 12). AAVCFTR virus production was also observed in Hela clone 37 cells, but not in parental Hela cells, with adenovirus alone (FIG. 7, compare lane 6 and 4), consistent with the observed increase in AAVCFTR signal in DNA isolated from these cells in FIG. 6, lane 4. The difference in intensity of the hybridization observed at 1.488 kb in lane 6 (FIG. 7) versus the signal representing input AAVCFTR virus (lanes 4, 7, 9–11) reveals the increase in AAVCFTR titer upon the infection and amplification of AAVCFTR in Hela clone 37 cells.

These results demonstrate that packaging cells, in the presence of adenovirus, can replicate and package rAAV vector genomes into infectious virions by either transfection or infection (FIGS. 6 and 7).

Example 11

Rescue and Amplification of an Integrated rAAV Vector from Packaging Cells

Packaging cells (derived from Hela clone 37) were electroporated as previously described with a recombinant AAV vector (designated rAAV-CMV-Hygro) containing the hygromycin resistance gene operably linked to the CMV enhancer/promoter; and a stable, polyclonal line was derived by selection in 300 µg/ml hygromycin.

Figure 8:
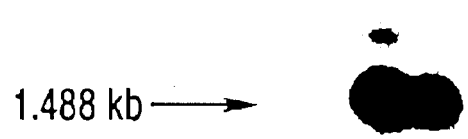
FIG. 8 is a reproduction of a Southern blot demonstrating that packaging cells produced according to the present invention possess sufficient rep activity to recognize, excise and amplify an integrated rAAV vector, as described in Example 11.

In order to determine whether the rep activity present in the packaging cells could effectively recognize, excise and amplify the integrated rAAV-CMV-Hygro vector, the polyclonal, hygro-resistant Hela clone 37 line ($2.5 \times 10^5$ cells/well) was seeded onto a 6 well dish for infection with adenovirus (MOI=50) alone, plus wild type AAV (MOI=5) or uninfected. After 48 hours, nucleic acid was prepared, as previously described, digested with NheI/Asp718 and Southern analysis performed using a labeled, 1048 bp NheI/Asp718 fragment containing the hygromycin resistance gene as the probe. FIG. 8 shows the result of this analysis. Lane 1 represents DNA isolated from the parental Hela clone 37 cell line, and hence does not contain the hygro-resistance gene. Lane 2 contains DNA from the polyclonal, hygro-resistant Hela clone 37 line which at this exposure time does not show the presence of the resistance gene which is present at an average of about 1 copy/well (data not shown). DNA isolated from a duplicate well containing the hygro-resistant Hela clone 37 cells treated with adenovirus was run in lane 3. The hybridization present at 1048 bp represents material derived from the excision and amplification of the integrated AAVCMVHygro vector integrated in the Hela clone cells. The addition of wild-type AAV to the adenovirus infection gave similar results (lane 4).

These results demonstrate that the rep activity generated in the rAAV packaging cells is sufficient to recognize, excise and amplify an integrated recombinant AAV vector.

What is claimed is:

1. A method of producing a mammalian cell for packaging of a recombinant AAV (rAAV) vector, said method comprising:

replicating a mammalian cell to produce a population of cells; wherein the mammalian cell comprises a stably integrated AAV cap gene operably linked to AAV p40 promoter, and a stably integrated AAV rep gene operably linked to a helper virus-inducible heterologous promoter, wherein (a) the AAV cap gene and the AAV rep gene are stably integrated into the mammalian cell's genome; (b) p5 promoter function has been replaced by the helper virus-inducible heterologous promoter; (c) said mammalian cell was prepared by introducing a plasmid comprising both AAV rep and AAV cap arranged as in the AAV genome into the mammalian cell; and (d) upon introduction of a helper virus into the population of the cells, said cells exhibit helper virus-inducible expression of said stably integrated AAV rep gene.

2. The method according to claim 1, wherein said helper virus is an adenovirus.

3. The method according to claim 1, wherein said mammalian cell grows at least one half as rapidly as parental-type cells that do not contain an AAV rep gene, and wherein said mammalian cell when used to package rAAV vectors produces at least 100 rAAV particles/cell.

4. The method according to any of claims 1–3, wherein said heterologous promoter is a mouse metallothionein I (mMT-I) promoter.

5. A cell produced by the method of claim 1, and progeny thereof.

6. A cell produced by the method of claim 3, and progeny thereof.

7. A cell produced by the method of claim 4, and progeny thereof.

8. A mammalian cell for packaging of a recombinant AAV (rAAV) vector, said cell comprising a stably integrated cap gene operably linked to AAV p40 promoter, and a stably integrated rep gene operably linked to a helper virus-inducible heterologous promoter; wherein (a) the cap gene and the rep gene are stably integrated into the mammalian cell's genome; (b) p5 promoter function has been replaced by the helper virus-inducible heterologous promoter; (c) said cell exhibits helper-virus-inducible expression of said stably integrated AAV rep gene; and (d) said mammalian cell was prepared by introducing a plasmid comprising both rep and cap arranged as in the AAV genome into the mammalian cell.

9. The AAV packaging cell of claim 8, wherein said helper-virus-inducible expression of said stably integrated AAV rep gene is inducible by adenovirus.

10. The AAV packaging cell of claim 8, wherein said packaging cell grows at least one half as rapidly as parental-type cells that do not contain an AAV rep gene, and wherein said packaging cell when used to package rAAV vectors produces at least 100 rAAV particles/cell.

11. The AAV packaging cell of any of claims 8–10, wherein said heterologous promoter is a mouse metallothionein I (mMT-I) promoter.

12. The AAV packaging cell of claim 8, further comprising a stably integrated recombinant AAV (rAAV) vector, said vector comprising a polynucleotide sequence of interest located between two AAV inverted terminal repeat (ITR) regions, wherein said polynucleotide is operably linked to a promoter.

13. A method of packaging a recombinant AAV vector, comprising:

incubating the AAV packaging cell of claim 8 under conditions suitable for replication and packaging of AAV; wherein the AAV packaging cell further comprises: (a) an rAAV vector comprising a polynucleotide sequence of interest located between two AAV inverted terminal repeat (ITR) regions, wherein said polynucleotide is operably linked to a promoter; and (b) a helper virus; wherein the incubation results in packaged rAAV vector.

14. A method of packaging a recombinant AAV vector, comprising:

incubating the AAV packaging cell of claim 12 under conditions suitable for replication and packaging of AAV; wherein the AAV packaging cell further comprises a helper virus; wherein the incubation results in packaged rAAV vector.

15. A method of determining the infectious titer of an rAAV vector preparation, comprising:

(a) introducing a helper virus and serial dilutions of an rAAV vector preparation to the AAV packaging cells of claim 8;

(b) incubating the cells under conditions suitable for replication of AAV; and (c) determining the amount of replicated rAAV vector relative to an rAAV preparation of known titer.

16. A method of producing a mammalian cell for packaging of a recombinant AAV (rAAV) vector, said method comprising:

introducing a plasmid comprising both AAV rep and AAV cap arranged as in the AAV genome into a mammalian cell, wherein the AAV cap gene is operably linked to AAV p40 promoter and the AAV rep gene is operably linked to a helper virus-inducible heterologous promoter, wherein p5 promoter function has been replaced by the helper virus-inducible heterologous promoter; wherein the plasmid becomes stably integrated into the mammalian cell's genome; and wherein said cell exhibits helper virus-inducible expression of said stably integrated AAV rep gene.

17. The method according to claim 16, wherein said helper virus-inducible expression of said stably integrated AAV rep gene is inducible by adenovirus.

18. The method according to claim 16, wherein said mammalian cell grows at least one half as rapidly as parental-type cells that do not contain an AAV rep gene, and wherein said mammalian cell when used to package rAAV vectors produces at least 100 rAAV particles/cell.

19. The method according to any of claims 16–18, wherein said heterologous promoter is a mouse metallothionein I (mMT-I) promoter.

20. A cell produced by the method of claim 18, and progeny thereof.

21. A method of packaging a recombinant AAV vector, comprising:

incubating the AAV packaging cell of claim 20 under conditions suitable for replication and packaging of AAV; wherein the AAV packaging cell further comprises: (a) an rAAV vector comprising a polynucleotide sequence of interest located between two AAV inverted terminal repeat (ITR) regions, wherein said polynucleotide is operably linked to a promoter; and (b) a helper virus; wherein the incubation results in packaged rAAV vector.

22. The method of claim 21, wherein said helper virus is an adenovirus.

* * * * *